US007906962B2

(12) United States Patent
Han et al.

(10) Patent No.: US 7,906,962 B2
(45) Date of Patent: Mar. 15, 2011

(54) DYNAMIC NUCLEAR POLARIZATION ENHANCED NUCLEAR MAGNETIC RESONANCE OF WATER UNDER AMBIENT CONDITIONS

(75) Inventors: Songi Han, Santa Barbara, CA (US); Evan R. McCarney, Wellington (NZ); Brandon D. Armstrong, Santa Barbara, CA (US); Ravinath Kausik, Goleta, CA (US); Hanna Pavlova, Goleta, CA (US); Mark Lingwood, Goleta, CA (US); Elliott Brown, Glendale, CA (US)

(73) Assignee: The Regents of the University of California, Oakland, CA (US)

( * ) Notice: Subject to any disclaimer, the term of this patent is extended or adjusted under 35 U.S.C. 154(b) by 117 days.

(21) Appl. No.: 12/229,540

(22) Filed: Aug. 25, 2008

(65) Prior Publication Data

US 2009/0121712 A1     May 14, 2009

Related U.S. Application Data

(60) Provisional application No. 60/966,117, filed on Aug. 24, 2007, provisional application No. 61/132,384, filed on Jun. 18, 2008, provisional application No. 61/010,467, filed on Jan. 9, 2008.

(51) Int. Cl.
*G01V 3/00* (2006.01)
(52) U.S. Cl. .......................................... 324/307; 324/300
(58) Field of Classification Search .......... 324/300–322; 600/410–435
See application file for complete search history.

(56) References Cited

U.S. PATENT DOCUMENTS

| 5,840,701 | A | 11/1998 | Hsia | |
|---|---|---|---|---|
| 6,876,877 | B2 | 4/2005 | Eden | |
| 7,495,435 | B2 * | 2/2009 | Appelt et al. | 324/300 |
| 7,639,007 | B2 * | 12/2009 | Hutton et al. | 324/307 |
| 2007/0025918 | A1 | 2/2007 | Hurd | |

OTHER PUBLICATIONS

Alecci, M., I. Seimenis, et al. (1998). "Nitroxide free radical clearance in the live rat monitored by radio-frequency CW-EPR and PEDRI." Physics in Medicine & Biology 43(7): 1899-1905.
Ardenkjaer-Larsen, J. H., B. Fridlund, et al. (2003). "Increase in signal-to-noise ratio of > 10,000 times in liquid-state NMR." Proceedings of the National Academy of Sciences of the United States of America 100(18): 10158-10163.

(Continued)

*Primary Examiner* — Melissa J Koval
*Assistant Examiner* — Dixomara Vargas
(74) *Attorney, Agent, or Firm* — Berliner & Associates

(57) ABSTRACT

A method and apparatus are provided for treating hydrated material in a fluid that contains water in which a stable nitroxide is attached to the hydrated material. A dynamic nuclear polarization process (DNP) is conducted on the hydrated material whereby to hyperpolarize the water. A polarization cell contains the hydrated material to obtain hyperpolarized water free from the nitroxide. The dynamic nuclear polarization process is conducted using components comprising a tunable, solid state high power X-band driver and an X-band resonator for microwave transmission to the hydrated material. The components can also include a radio-frequency nuclear magnetic resonance probe, a permanent magnet formed to receive the hydrated material, a portable nuclear magnetic resonance spectrometer, and an electron spin resonance detector. The components can be sized to be portable, and include electrical input and output and a lap-size hardcase with access to the electrical input and output.

15 Claims, 11 Drawing Sheets

OTHER PUBLICATIONS

Ardenkjaer-Larsen, J. H., I. Laursen, et al. (1998). "EPR and DNP properties of certain novel single electron contrast agents intended for oximetric imaging." Journal of Magnetic Resonance 133(1): 1-12.

Armstrong, B. D. and S. Han (2007). "A new model for Overhauser enhanced nuclear magnetic resonance using nitroxide radicals." The Journal of Chemical Physics 127(10): 104508-10.

Armstrong, B. D., M. D. Lingwood, et al. (2008). "Portable X-band system for solution state dynamic nuclear polarization." Journal of Magnetic Resonance 191(2): 273-281.

Borah, B. and R. G. Bryant (1981). "NMR Relaxation Dispersion in an Aqueous Nitroxide System." Journal of Chemical Physics 75(7): 3297-3300.

David J. Lurie, H. L., Sergey Petryakov, Jay L. Zweier, (2002). "Development of a PEDRI free-radical imager using a 0.38 T clinical MRI system." Magnetic Resonance in Medicine 47(1): 181-186.

Fukuda, H., A. Goto, et al. (2001). "Electron spin resonance study of the pH-induced transformation of micelles to vesicles in an aqueous oleic acid/oleate system."Langmuir 17(14): 4223-4231.

Gitti, R., C. Wild, et al. (1988). "Solid-liquid intermolecular transfer of dynamic nuclear polarization. Enhanced flowing fluid proton NMR signals via immobilized spin labels." Journal of the American Chemical Society 110(7): 2294-2296.

Hausser, K. H. and D. Stehlik (1968). "Dynamic nuclear polarization in liquids." Advances in Magnetic Resonance 3: 79-139.

Krishna, M. C., S. English, et al. (2002). "Overhauser enhanced magnetic resonance imaging for tumor oximetry: Coregistration of tumor anatomy and tissue oxygen concentration." Proceedings of the National Academy of Sciences of the United States of America 99(4): 2216-2221.

McCarney, E. R., B. D. Armstrong, et al. (2008). "Dynamic Nuclear Polarization Enhanced Nuclear Magnetic Resonance and Electron Spin Resonance Studies of Hydration and Local Water Dynamics in Micelle and Vesicle Assemblies." Langmuir 24(18): 10062-10072.

McCarney, E. R., B. D. Armstrong, et al. (2007). "Hyperpolarized water as an authentic magnetic resonance imaging contrast agent." Proceedings of the National Academy of Sciences of the United States of America 104(6): 1754-1759.

McCarney, E. R. and S. Han (2008). "Spin-labeled gel for the production of radical-free dynamic nuclear polarization enhanced molecules for NMR spectroscopy and imaging." Journal of Magnetic Resonance 190(2): 307-315.

Nicholson, I., D. J. Lurie, et al. (1994). "The Application of Proton-Electron Double-Resonance Imaging Techniques to Proton Mobility Studies." Journal of Magnetic Resonance Series B 104(3): 250-255.

Wind, R. A. and J. H. Ardenkjaer-Larsen (1999). "H-1 DNP at 1.4 T of water doped with a triarylmethyl-based radical." Journal of Magnetic Resonance 141(2): 347-354.

Wolber, J., F. Ellner, et al. (2004). "Generating highly polarized nuclear spins in solution using dynamic nuclear polarization." Nuclear Instruments & Methods in Physics Research Section a-Accelerators Spectrometers Detectors and Associated Equipment 526(1-2): 173-181.

* cited by examiner

EXAMPLE NITROXIDE SPIN LABEL

EXAMPLE MEMBRANE PROTEIN

EXAMPLE PROTEIN AGGREGATE (PARALLEL STACKING)

EXAMPLE SURFACTANT VESICLE

EXAMPLE SURFACTANT MICELLE

THIS METHOD IS APPLICABLE TO LIPID BILAYER MEMBRANES AND OTHER BIOLOGICAL SOFT MATTER

DYNAMIC NUCLEAR POLARIZATION ENHANCED NUCLEAR MAGNETIC RESONANCE OF WATER UNDER AMBIENT CONDITIONS

CROSS-REFERENCE TO RELATED APPLICATIONS

This application claims the benefit of Provisional Patent Application No. 60/966,117, filed Aug. 24, 2007, No. 61/010,467, filed Jan. 9, 2008, and No. 61/132,384, filed Jun. 18, 2008.

STATEMENT REGARDING FEDERALLY SPONSORED RESEARCH OR DEVELOPMENT

This invention was made with Government support under Grant Nos. DMR 00-80034, DMR 05-20415 and CHE-0645536, all from the National Science Foundation. The Government has certain rights in this invention.

FIELD OF THE INVENTION

The invention relates to methods and an apparatus for conducting a dynamic nuclear polarization process on hydrated materials under ambient conditions.

BACKGROUND OF THE INVENTION

"Water is the driver of nature." [Leonardo de Vinci] In a world where water is so ubiquitous and vital, the exchange and transport characteristics of water is fundamental for the function of an endless range of biological and industrial processes; blood physiology, protein folding, plant metabolism, biomaterial function, and oil recovery from reservoir rocks are only drops in the bucket. In nature the interaction of water with surfactants, phospholipids or proteins plays an important role in membrane stability and function, which determine important characteristics such as permeability to small molecules and insertion susceptibility to proteins and other biomolecules [14-20]. Water content and dynamics play a key role in micelle-vesicle systems, which were classically used as bioreactors and membrane mimetic systems, but are now going through a rebirth as drug delivery systems [21-24].

However, there is a paucity of analytical tools that are capable of directly tracing and quantifying the transport and function of water through these already water-saturated materials in a non-invasive and chemically selective manner. While there have been many studies on boundary layer water coupled to or interacting with the surface of interfacial or protein molecular assemblies [17, 25-28] (e.g. by IR and near-IR vibrational spectroscopy [28] and magnetic resonance methods [17, 26, 27]), the characterization of surface water that is weakly interacting with the surface or the internal water of the fluidic (hydrophobic) interior of micelle, vesicle, or membraneous materials is sparse [18, 29-31] because dynamic water is more challenging to characterize with the current spectroscopic and analytic techniques. The importance of and interest in water, but also the difficulty in the experimental assessment of local water dynamics, can be recognized by the fact that there was a 5-days symposium as part of the most recent American Chemical Society meeting (August 2008, Philadelphia) focused only on water-mediated interactions, and that >90% of the talks were theory or simulation-based studies.

The in vitro and in vivo analysis of biological samples greatly relies on non-invasive spectroscopic techniques, non-disturbing probe molecules and the capability to perform measurements of bulk fluid samples under ambient biological conditions. Nuclear magnetic resonance (NMR) is, according to these criteria, a superior tool for providing detailed molecular signatures and images utilizing very low-energy radio frequency (RF) irradiation (10-900 MHz) and endogenous probes (e.g. $^1$H) of the biological sample that inhere sufficiently long coherence times to allow for analysis at ambient temperatures. Magnetic resonance imaging (MRI) is capable of producing images of the entire human body by employing the $^1$H signal of the most abundant molecule in biology, water, as its probe species. However, both NMR and MRI suffer from signal overlap of the abundant endogenous probes and low sensitivity. So, while NMR is well suited to non-invasively elucidate molecular details of bulk soft matter contained in water under ambient conditions [17, 32], it does not provide differentiable frequencies for distinct water species, such as bulk, boundary, or interior water molecules. In addition, the slower tumbling of larger structures and the magnetic susceptibility mismatch due to interfaces in multiphase systems (emulsions, micelles, vesicles, etc.) contribute to NMR line broadening and result in poor resolution.

NMR studies, despite these challenges, have quantified ordering of boundary and interbilayer water [14, 27, 33-35] through measurements of quadrapolar splitting of $D_2O$ probe species, and $^1$H nuclear Overhauser spectroscopy (NOESY) cross-relaxation measurements have measured water residence (<5 Å) on lipid chain segments [17, 35, 36] or proteins [15, 16, 37]. Some $^1$H NOESY studies have measured the residence time for water, e.g. in lipid layers to be ≦100 ps [25], which is related to bulk water exchange properties of lipid assemblies. So, NMR and MRI are still one of the best tools for studying solution and soft matter samples, but it faces two main challenges. One is the lack of sensitivity, inherent to all NMR experiments, especially for in vivo but also for in vitro NMR studies of transport in biological and biomedical samples. The other challenge is the lack of contrast, e.g., between the water molecules to be traced and the bulk water or water containing specimen. Paramagnetic molecules or ions are usually added to provide the water of interest with a different, detectable, physicochemical property, and ultimately the desired contrast. Dynamic susceptibility contrast-enhanced imaging (DSC), a widely used MRI approach for in vivo cardiovascular perfusion imaging, uses stable Gadolinium chelates. However, such tracers are invasive and somewhat toxic and do not precisely reflect the properties of water. Existing methodologies to achieve "authentic" contrast are based on modulation of the polarization of inflowing water to distinguish it from the bulk water (NMR angiography [1], NMR time-of-flight remote detection [2]), but the limitation is that the maximum modulation obtained is through the inversion of polarization, which corresponds to a small contrast. Additionally, the NMR phase can be utilized to distinguish between still and moving molecules (the principle of obtaining velocity or diffusion maps by NMR [3]), but it is not sensitive to time-variant flow dispersion evolving in time and space.

Another powerful approach is electron spin resonance (ESR) of soft molecular assemblies through the incorporation of monomer lipid units that are spin-labeled at different sites. ESR line shape analysis provides rotational correlation times and anisotropy order parameters of spin labeled lipid segments [26, 38-41].

Electron spin echo envelope modulation (ESEEM) studies map the interaction between chain segments and heavy water by replacing water with $D_2O$, in turn providing quantitative information on water penetration characteristics in membrane systems [42-44]. Although ESEEM provides a detailed analysis of water penetration in ordered membranes with resolution at the level of lipid chain positions, the freezing process can force water out of the hydrophobic core and result in different hydration properties compared to the fluid state [29]. ESR measurements of the $^{14}$N hyperfine splitting constants, $a_N$, and the g tensor element $g_{xx}$ of spin labeled lipid chains are sensitive to polarity profiles, reflect interbilayer water distribution [18, 29-31], and can be performed on fluid samples for a wide range of temperatures. Literature studies model the $a_N$ parameter, e.g. for oxazolidine-N-oxyl (doxyl) spin probes in fluid membranes, to determine hydrogen-bonding contribution in terms of fractional increments relative to pure water in terms of water content [29, 45]. These are relatively new methodologies and require low temperature reference measurements or high-frequency ($\geq$95 GHz) ESR techniques, but have important potential. However, the interpretation of $a_N$ often does not sufficiently discriminate between the extent of hydrogen bonding due to changing water content and the local solvent polarities or the motional anisotropy [29-31, 46].

Neutron and X-ray diffraction are also important techniques for studying hydration on bilayers [17, 25]. Diffraction methods are advantageous because they provide information about water density with lipid chain resolution normal to the bilayer without the use of spin labels. However again, it is challenging to employ these techniques to study bilayers with liquid crystalline mobility, and impossible to study dynamic micelle or vesicle systems. New and complementary analysis techniques are greatly needed, given the importance and difficulty of studying the bulk interfacial fluid dynamics of soft assemblies.

So, in summary, although NMR MRI are superior tools for providing detailed molecular signatures or images utilizing very low-energy radio frequency irradiation (10-900 MHz) and endogenous probes (e.g. $^1$H) of the biological sample for analysis at ambient temperatures, both techniques suffer from signal overlap of the abundant endogenous probes and low sensitivity. ESR, a sister technique to NMR, utilizes the much stronger magnetic moment of the electron spins for signal (approximately 660 times stronger than proton), but requires the presence of unpaired electrons. For diamagnetic biological samples, this is achieved by attaching stable nitroxide radicals, called spin-labels, to the molecule of interest, thus no direct signatures from the molecule of interest is utilized. Dynamic nuclear polarization (DNP) presents a mechanism to transfer part of the orders of magnitude larger electron spin polarization of radical species to nuclear spin polarization, thus greatly amplifying the NMR and MRI signal, leading to increased sensitivity and/or contrast. There are four DNP processes that can transfer polarization from electron to nuclear spins; the Overhauser Effect [77], solid effect [78], thermal mixing [79], and the cross effect or electron-nuclear cross polarization (eNCP) [80]. The latter three can be effective at the high magnetic fields required for NMR spectroscopy, which technique is becoming more developed, known and even commercially available because of its unique and important potential [81, 82], despite the fact that it requires complex and expensive technology.

The first, the Overhauser effect, is the main DNP mechanism that the methods and apparatus of this invention utilize. The Overhauser effect driven DNP method has found applications in the imaging field with Overhauser enhanced magnetic resonance imaging (OMRI) [83-88], remotely enhanced liquids for imaging contrast (RELIC) [89], and determining local viscosities near a spin-labeled micelle from changes in the Overhauser enhancement [90].

The efficiency of the Overhauser effect decreases with field [91], however it is still effective at the relatively easy to handle X-Band electron spin frequencies at 0.35 Tesla [92]. Although methods in this invention are not limited to the use of X-band, all proof of principles of this invention have been demonstrated at X-band and the apparatus of this invention relies on X-band hardware. High-power amplifiers have long been important in X-band systems, particularly tactical radar and satellite communications (SATCOMM) systems for military and government applications. X-band is usually chosen for these systems as a compromise between range and resolution. Good range is achieved provided that the transmitter and receiver are linked "line-of-sight", and there is sufficient transmit power to maintain some "link margin." Starting in the 1950s, effective tactical radar systems were engineered with vacuum-tube power amplifiers to boost the transmit power to the range of 10 W or higher depending on the required frequency range. The vacuum-tube of choice rapidly became the traveling wave tube amplifier (TWTA) because of its excellent bandwidth, linearity, low noise, and high power. The TWTA continued as the workhorse X-band power amplifier for decades, even after the advent of solid-state electronics in the 1960s and 70s because solid-state power amplifiers (SSPAs) could not achieve the power levels, bandwidth, or both, to meet radar and SATCOMM systems requirements.

Starting in the 1990s, SSPAs advanced to the point where they could compete with TWTAs in X-band systems. The key breakthrough was the invention of efficient amplifiers made from GaAs field-effect transistors in the form of monolithic microwave integrated circuits (MMICs). GaAs MMICs allowed the power levels from single X-band amplifiers to be increased from the 1-W level to the 10-W level. And as in all IC-based components, the cost of these amplifiers dropped dramatically, falling far below the cost of any TWTA on the market. By the mid 1990s, GaAs MMIC amplifiers were being manufactured by Texas Instruments and later, by TriQuint, with 10-W output power capability and with good instantaneous bandwidth, spanning across the full X band range (8-to-12 GHz). In parallel but lagging behind, X-band solid-state electronics began to disseminate into other applications areas such as commercial collision avoidance radar and electron spin resonance (ESR) spectroscopy. But none of these appeared to take full advantage of the electronics being developed for military and government systems, in large part because of legacy designs and a shortage of RF engineering talent, much of which was employed by DOD contractors or SATCOMM companies.

RF switches have also been important in radar and communications systems since their early days for transmit pulse control. However pulse widths never had to be decreased much below ~1 microsecond. So, early radar and SATCOMM systems used vacuum-based or magnetic (ferrite) switches, and these were replaced by solid-state switches in the 1960s and 1970s in the form of PIN diodes. PIN diode switches are not very fast (0.1 microsecond being the best), but have good power handing (>1 W) and low cost. So PIN diodes became the preferred switch technology into the 1990s. Then along came switches based on field-effect transistors, especially pseudomorphic high-electron mobility transistors (pHEMTs). pHEMTs offered very low insertion loss and lower activation voltage than PIN diodes, but also ease of integration and low cost. pHEMT switches became available as MMICs, similar to those utilized in SSPAs, and were quickly integrated with power transistors to form transmit-receive (T/R) module chips. The T/R MMICs incorporated switching power amplification, low-noise amplification and other RF functionality, so became the mainstay for solid-state tactical radar at X-band and beyond.

BRIEF SUMMARY OF THE INVENTION

A method and apparatus are provided for utilizing and studying hydrated materials in a fluid that contains water in which a stable nitroxide spin label is covalently attached to the hydrated material. A dynamic nuclear polarization (DNP) process following the Overhauser mechanism is conducted on the hydrated material whereby to hyperpolarize the water. A polarization cell contains the hydrated material to obtain hyperpolarized water that does not dissolve the nitroxide radical as the radical is covalently and stably attached to the hydrated material. The DNP process is conducted using components comprising a tunable, solid state, high power, X-band driver and an X-band resonator for microwave transmission to the hydrated material to irradiate the electron spin resonance (ESR) transitions of the nitroxide radicals attached to the hydrated materials. The DNP instrumentation setup can also include a radio-frequency nuclear magnetic resonance (NMR) probe, a magnet in which to place the hydrated material and the X-band resonator to allow for magnetic resonance analysis, a NMR spectrometer, and an ESR detector. All components (X-band driver, NMR probe, magnet, NMR spectrometer and ESR detector) can be sized to be a portable DNP instrument.

This invention surmounts both challenges of low sensitivity and contrast of magnetic resonance analysis and imaging by introducing highly enhanced $^1$H signal of water as a novel contrast agent to (1) quantify the dynamic interaction/collision between the spin label and water and (2) to quantify and visualize the development of flow patterns and dispersion by NMR imaging upon injection of hyperpolarized water. The unique features of the former is that the spin label is attached to the hydrated materials at specific sites (e.g. at a specific aminoacid of a protein or a specific hydrocarbon chain position of a polymer, surfactant or lipid), that very local water dynamics within 5-10 Å distance of the spin label is detected, and that high signal amplification of the water NMR signal allows for the study of minute samples quantities (a few μl) and dilute systems (e.g. 100-500 μM spin label concentration). These features altogether allow the experimental measurements of very local water dynamics of surfaces and interiors of hydrated materials (proteins, membranes, micelles or polymers) under ambient conditions contained in bulk water, which is an unparalleled technological capability. For the latter, providing contrast through the hyper-polarization of $^1$H nuclear spins of water is a non-invasive method because the physicochemical property of water remains unchanged, the same way as the function of water that is thermally polarized in a magnetic field of an MRI scanner is not altered from that in our earth's magnetic field. In order to apply this signal enhancement to biological samples or even in vivo, it is crucial to eliminate radicals from the polarized molecules prior to injection or detection. We present affinity chromatography media covalently spin-labeled via stable amide bonds that disperses the radicals in sufficiently high concentration and mobility without permitting their release into the biological sample. We demonstrate the efficiency of this ideal polarization matrix for the direct DNP enhancement of the $^1$H signal of water in continuous-flow under ambient conditions at 0.35 T fields. However, our methodology can be utilized at and applied to at very low magnetic fields (e.g. earth's magnetic field, 5, 15 or 50 Gauss) up to high magnetic fields (e.g. 1, 1.5, 3, 7 or 9 Tesla). So, although we demonstrated the utility of our method and apparatus at 0.35 T using X-band ESR, our method and apparatus is not limited to this field and ESR frequency.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
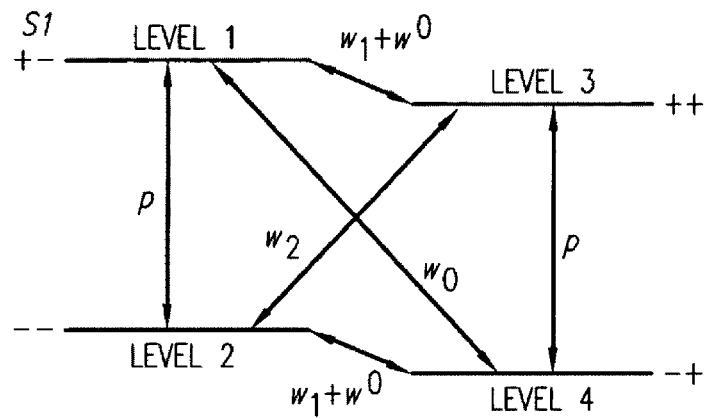
FIG. 1 is 4-level energy diagram for 2 coupled spin=½ systems, appropriate for an electron-proton system. $w_1$, $w_0$, and $w_2$ are the dipolar spin relaxation transitions, $w^o$ is the intrinsic nuclear spin transition, and p is the intrinsic electron spin transition.

The present invention provides a method and apparatus for treating hydrated materials in a fluid that contains water in which a stable nitroxide is attached to the hydrated material. The DNP process is conducted on the hydrated material to hyperpolarize the water. The DNP process is conducted in a polarization cell (i.e. a ESR cavity of some kind) that contains the hydrated material wherein the hyperpolarized water is obtained, where the nitroxide radical is not freely dissolved in water, which allows for the ready separation of water and the nitroxide radical, if needed. In particular embodiments, the hydrated material in the polarization cell is nitroxide functionalized sepharose and the nitroxide is 2,2,6,6-tetramethypiperidine 1-oxyl. The hydrated material can also be other hydrated gels or polymers besides sepharose, such as hydrogel, tentagel, sephadex or modifications of agarose materials. In another particular embodiment, nitroxide radicals are covalently attached to targeted sites on the hydrated material to form a functionalized, i.e. spin labeled, molecule or material that is dissolved or suspended in water. In this embodiment, the hydrated material can be composed of peptides, proteins, lipid molecules, amphiphilic surfactants, or polymers. Here, DNP is used to amplify only the $^1$H NMR signal of the local environment of the spin label that is specifically attached to the hydrated materials at a specific site of interest. The method and apparatus can selectively detect local water at the location of the spin label associated with the hydrated material suspended in bulk water, because the local water will provide a certain $^1$H NMR signal amplification factor through DNP, from which number the translational water dynamics can be extracted. Here, the $^1$H NMR signal amplification factor through DNP depends on the extent of dynamic dipolar coupling between the electron spins residing on the spin labeled molecules which possess greater than 600 fold higher spin polarization compared to $^1$H nuclei and the $^1$H nuclei of the water. In another embodiment, the DNP process is conducted using components comprising a tunable, solid state high power X-band driver and an X-band resonator for microwave transmission to the hydrated material. The DNP instrumentation setup can also include a radio-frequency nuclear magnetic resonance probe, a magnet to place the hydrated material that allows the magnetic resonance analysis, a nuclear magnetic resonance spectrometer, and an electron spin resonance detector. In a further embodiment, the key components are sized to enable the DNP device to be portable wherein the device includes electrical input and output and including a lap-size hard-case with access to the electrical input and output in which the components are packaged.

This invention surmounts both challenges of low sensitivity and low contrast of certain aspects of magnetic resonance analysis by introducing highly enhanced $^1$H signal of water as a novel contrast agent to quantify the water dynamics (e.g. local diffusion coefficient) at a specific molecular location of hydrated materials, averaged over a local volume within 5-10 Å distance from the spin label, and to visualize the development of flow patterns and dispersion by NMR imaging. Providing contrast through the hyper-polarization of $^1$H nuclear spins of water is a non-invasive method because the physico-chemical property of water remains unchanged, the same way as the function of water that is thermally polarized in a magnetic field of an MRI scanner is not altered from that in our earth's magnetic field. In order to apply this hyperpolarized water to biological samples or even in vivo, it is crucial to eliminate radicals from the polarized molecules prior to injection or detection. We present affinity chromatography media covalently spin-labeled via stable amide bonds that disperses the radicals in sufficiently high concentration and mobility without permitting their release into the biological sample. We demonstrate the efficiency of this ideal polarization matrix for the direct DNP enhancement of the $^1$H signal of water in continuous-flow under ambient conditions at 0.35 T fields.

There are three broad embodiments to the invention, which will be presented one after the other.

First Embodiment

Brief Description of Dynamic Nuclear Polarization

An in-depth description of the Overhauser effect can be found in several references [77, 91, 93, 94], and is discussed above in describing the second embodiment. For convenience, a brief summary relevant for free radicals dissolved in solution and free radicals attached to other molecules dissolved in solution will be further provided here. The Overhauser effect is typically described with the four level energy diagram shown in FIG. 1, where S represents an electron spin and I represents a nuclear spin (often a proton). Through dipolar and/or scalar coupling, the cross relaxation terms $w_o$ and $w_2$ (defined in FIG. 1) are non-zero, thus creating a non equilibrium distribution of S spins by irradiating it's transition can result in signal enhancement of the I spin. This enhancement, E, defined as $\langle I_z \rangle / \langle I_o \rangle$, where $\langle I_o \rangle$ is the equilibrium polarization is given by [91, 95]:

$$E = 1 - \rho f s \frac{|\gamma_S|}{\gamma_I}, \text{ where} \quad (1)$$

$$\rho = \frac{w_2 - w_o}{w_o + 2w_1 + w_2}, \quad (2)$$

$$f = \frac{w_o + 2w_1 + w_2}{w_o + 2w_1 + w_2 + w^o} = \frac{kCT_{10}}{1 + kCT_{10}} = 1 - \frac{T_1}{T_{10}}, \quad (3)$$

and on resonance of the S transition, $$s = \frac{AP}{1 + BP}. \quad (4)$$

The coupling factor, $\rho$, expresses the efficiency of dipolar or scalar coupling between the electron and nucleus and can vary between 0.5 for pure dipolar coupling and $-1$ for pure scalar coupling [91]. The leakage factor, f, depends on the concentration of the free radical relaxing the nuclei and can be easily determined by measuring the longitudinal relaxation times of the solvent with ($T_1$) and without ($T_{10}$) the presence of the free radical. As seen in Eq. 3, $f \rightarrow 1$ in the limit of high radical concentrations, where "high" radical concentration is determined by the relaxivity constant, k, describing how effective the electron relaxes the nuclei compared to the nuclei's own relaxation mechanisms. The saturation factor, s, is a function of the applied radiation power driving the electron spin transition. Traditionally, the constants A and B are given by A=a/n and B=a, where a is a constant dependent on the electron spin relaxation times and n is the number of hyperfine lines in the ESR spectrum [95]. However, our findings were that A and B are generally not only functions of the number of hyperfine lines, but also of the Heisenberg electron spin exchange rate, intrinsic electron spin relaxation rate, and in the case of the commonly used nitroxide radicals, the nitrogen nuclear spin relaxation rate, as quantitatively detailed elsewhere [92]. In the limit of high microwave power $s \rightarrow A/B = s_{max}$, which can vary between 1/n and 1 depending on the various factors listed above [92]. We use the terminology $E_{max}$ for the DNP enhancement factor (E) at the limit of infinite power.

DNP Enhancement of $^1$H Water

Figure 3A:
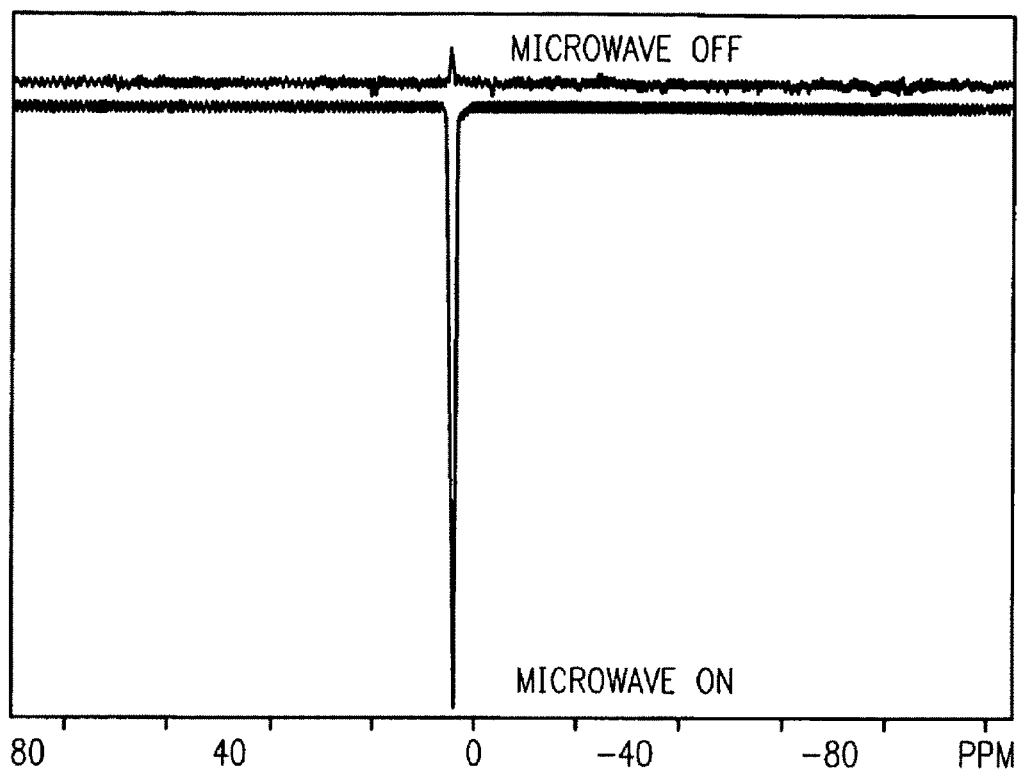
FIGS. 3A and B graphically depict the $^1$H NMR signal amplification of water and their change of amplitude as microwave irradiation is turned on and off.

With our current system using a magnetic field of 0.35 T, microwave frequency of 9.8 GHz and proton frequency of 14.8 MHz, we have successfully amplified the $^1$H NMR signal of water by a factor of $-130$ using 2,2,6,6-Tetramethylpiperidine 1-oxyl (TEMPO) derivatives as the free radical source and thus project the maximum enhancement to be around two orders of magnitude. The negative sign of the enhancement is due to the characteristics of dipolar relaxation governing the DNP enhancement [6] (see FIG. 3A). A 100-fold polarization in 0.35 Tesla field corresponds to thermal polarization achieved in a 35 Tesla magnet (21 Tesla currently being the highest magnetic field available for NMR experiments) which provides another perspective about the great potential of using the proposed methodology for producing hyper-polarized water.

The Usefulness of Matrix-Bound Stable Radicals

We developed matrix-bound stable radicals as the source for unpaired electrons, which possess highly efficient DNP performance in static and continuous-flow modes due to their high concentration and mobility in the sample solution, yet without separating themselves from the matrix into the flowing water. Radical-free $^1$H-hyperpolarized water can be created as it flows through the matrix and is continuously or pulse-wise fed into the system under investigation. The polarization matrix consist of TEMPO radicals that are conjugated to the agarose-based gel filtration matrix (SepharoseCL 4B, GE HealthCare) via stable covalent bonds, which leaves the flowing water radical-free as it flows out.

Immobilization Procedure of Matrix-Bound Stable Radicals

The TEMPO free radical was attached to NHS-Sepharose 4 Fast Flow (GE Healthcare) via a modified procedure provided by the manufacturer as follows: a spin label solution of 0.8 M 4-amino-TEMPO (Sigma-Aldrich) in 0.2 M $NaHCO_3$ and 0.5 M NaCl pH 8.3 buffer was prepared and stored at 4° C. The NHS-Sepharose media was washed with 10-15 volumes of 1 mM HCl at 4° C. The spin-labeling buffer containing 4-amino-TEMPO was added to the matrix and shaken over night at 4° C. The solution was rinsed with water and stored in 20% ethanol with a low concentration of 4-amino-TEMPO. The media was rinsed thoroughly with water before use. The N-hydroxysuccinimide ester reactive group of the sepharose reacts with the amine of 4-amino-TEMPO to produce a stable peptide bond as shown in below.

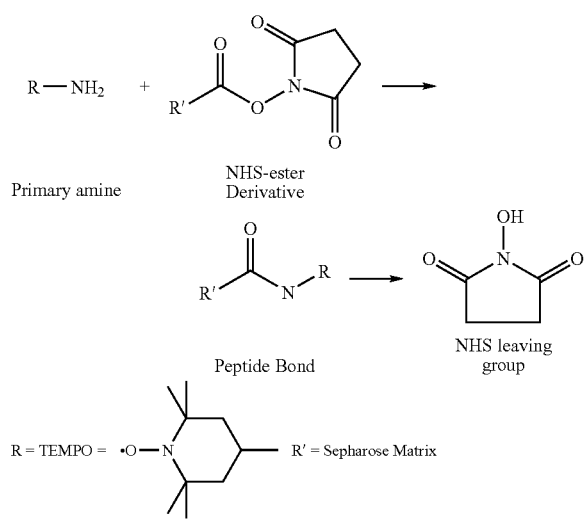

Water was pumped through a flow cell containing the spin-labeled polarization matrix where it gets hyperpolarized within a microwave cavity in the fringe field of an electromagnet. The hyperpolarized water then flows to the sweet spot of the magnet for NMR detection using a home built probe.

Flow Setup for $^1$H-Water Hyper-Polarization

Figure 2:
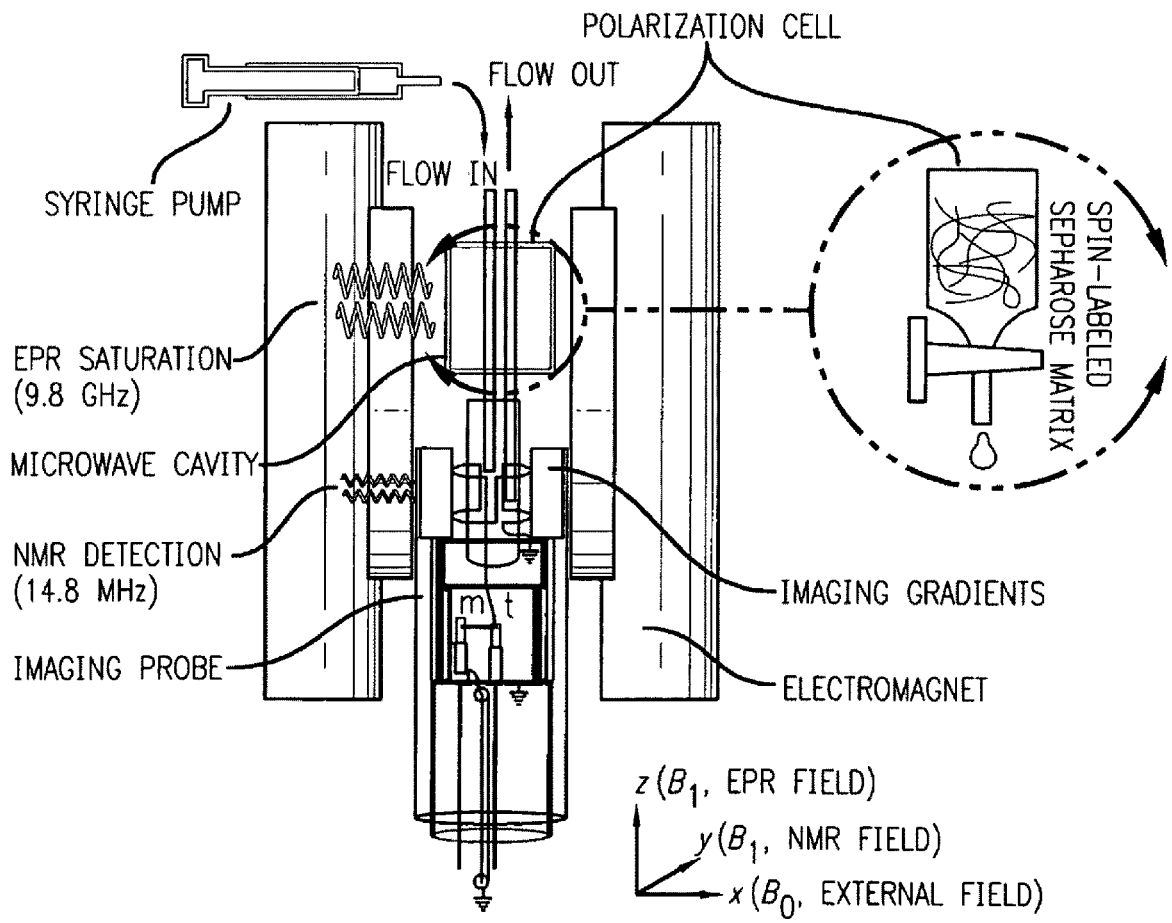
FIG. 2 is a schematic depiction of a setup for contrast MRI using hyper-polarized $^1$H water in continuous flow mode.

We setup a continuous-flow system that combines DNP polarization, water injection and NMR imaging to demonstrate NMR flow-contrast imaging using $^1$H hyperpolarized water. The radical-labeled sepharose matrix was loaded into a quartz reactor tube (2 mm OD, 1 mm ID) and was centered in the microwave cavity (Bruker Biospin, Billerica) at 0.34 T (FIG. 2). Using a syringe pump (KD Scientific, KDS200) we flow water through the radical-labeled polarization matrix inside a square cavity for X-band EPR (Bruker Biospin, Billerica) that obtains 200 mW microwave power with Q=1700. As water flows through the microwave cavity, the $^1$H of water becomes transiently hyperpolarized via the Overhauser effect (FIG. 2). The polarized water then entered the imaging cell through a septum and flowed through capillary tubing (0.8 mm OD, 0.6 mm ID) into the water reservoir where the perfusion images were obtained using a NMR imaging probe tuned to 14.8 MHz, and subsequently flows back out. The center of the imaging probe was separated from the center of the EPR cavity by 90 mm. The NMR experiment was carried out using the broadband channel of a Bruker Avance-300 spectrometer.

Performing Magnetic Resonance Imaging (MRI) Experiments in an Electromagnet

A commercial NMR probe (Bruker Biospin, Billerica Mass.) containing x, y and z-gradients designed for use in a main static magnetic field ($B_0$) oriented along the long axis of the probe (z axis) was employed for the imaging experiments in an EPR electromagnet, where the $B_0$ field is oriented perpendicular to the probe's long axis (FIG. 2). Therefore, instead of using the $dB_z/d_z$ and $dB_z/d_x$ component of the z- and x-gradients, their concomitant components $dB_x/d_x$ and $dB_x/d_z$ were utilized for our experiment (see supplemental information). In our current experimental setup, only imaging along the x and z axes can be performed because they gradient contains all three concomitant gradient components along the $B_{0,x}$ axis. This limitation is however due to our specific system and not of principle nature.

Model Samples to Test Contrast Imaging Using Hyperpolarized Water

Our technique of continuously hyper polarizing $^1$H-water allows for the visualization of characteristic flow vortices in flow reactors, heterogeneous flow dispersion in porous media packing of separation columns or perfusion pattern of physiological blood circulation. To demonstrate the potential applicability of our development, we spatially tracked the flow path of water in two different systems: one is a model reactor vessel with a characteristic geometry containing pure water and the other is a packing of water-saturated molecular sieves. In both cases, we visualized the macroscopic flow pattern (e.g. vortices, convection) for the former and mechanical dispersion for the latter, showcasing this novel methodology's capability to highlight water's flow path within water and water-saturated materials by NMR imaging.

Turning on and Off the $^1$H Contrast of Water by Control of DNP Polarization

Figure 3B:
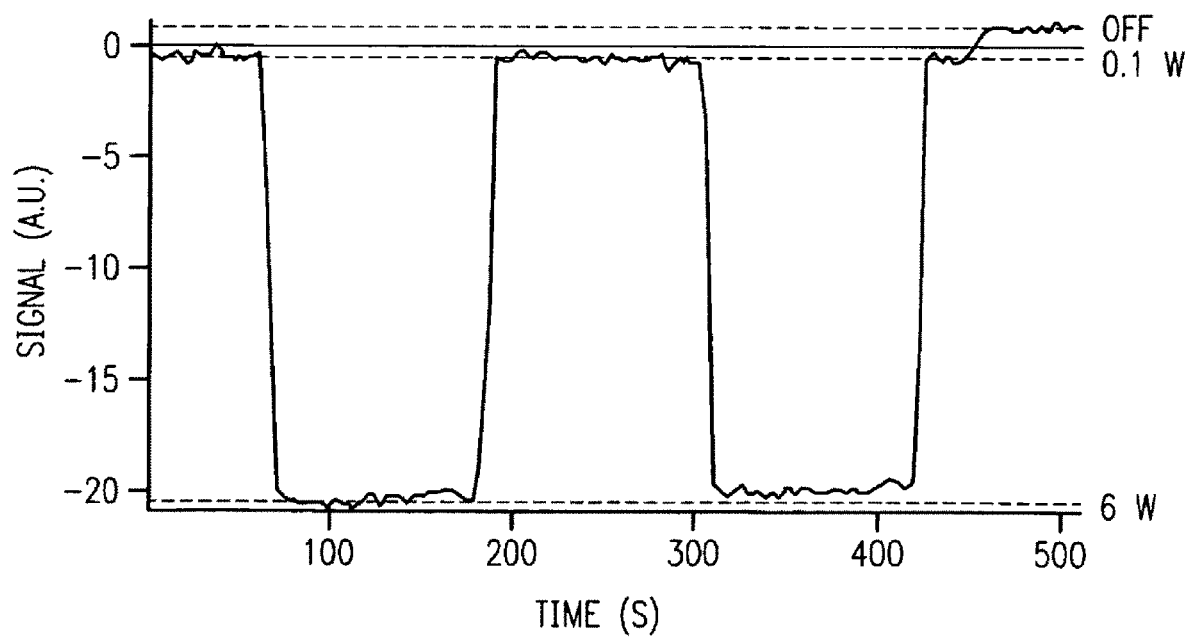

The characteristics of the polarization matrix allows for the near instantaneous (<1 s) and effective $^1$H polarization of water while continuously flowing at rates between 0.5 and 1.5 ml/min inside a 1 mm inner diameter column. The resonant microwave radiation is perpendicular to the flow of the water, allowing the water to enter at the top and exit through the bottom of the cavity. Because the water is radical-free it retains the hyper-polarization for the lifetime of the nuclear spin polarization of pure water, following an exponential decay with a time constant of ~2.7 s (spin-lattice relaxation time, $T_1$). By attenuating the microwave irradiation the hyperpolarization can be instantaneously turned off, and the $^1$H spin of water returns to its thermal equilibrium polarization at the magnetic field of 0.35 T. It is remarkable that the hyperpolarization, and therefore the NMR contrast can be turned on and off or even fine tuned by adjusting the microwave power. In FIG. 3B the observation of polarization over 8 minutes is depicted when we switched the microwave on and off to show that we could create different signals, thus contrast solely through the control of spin polarization. This is the basis of our statement that we are able to non-invasively control the contrast of the $^1$H NMR signal of water without changing its physicochemical property.

Referring to FIG. 3, upon microwave irradiation on resonant of the radical's EPR transition, the $^1$H NMR signal of water becomes negatively enhanced, which returns to the equilibrium value after the microwave irradiation was turned off (A,B). An event plot shows how NMR contrast of water can be turned on or off although the physically identical water is flowing through the NMR probe with time (B).

Description of Our Model Reactor Vessel Sample

Figure 4:
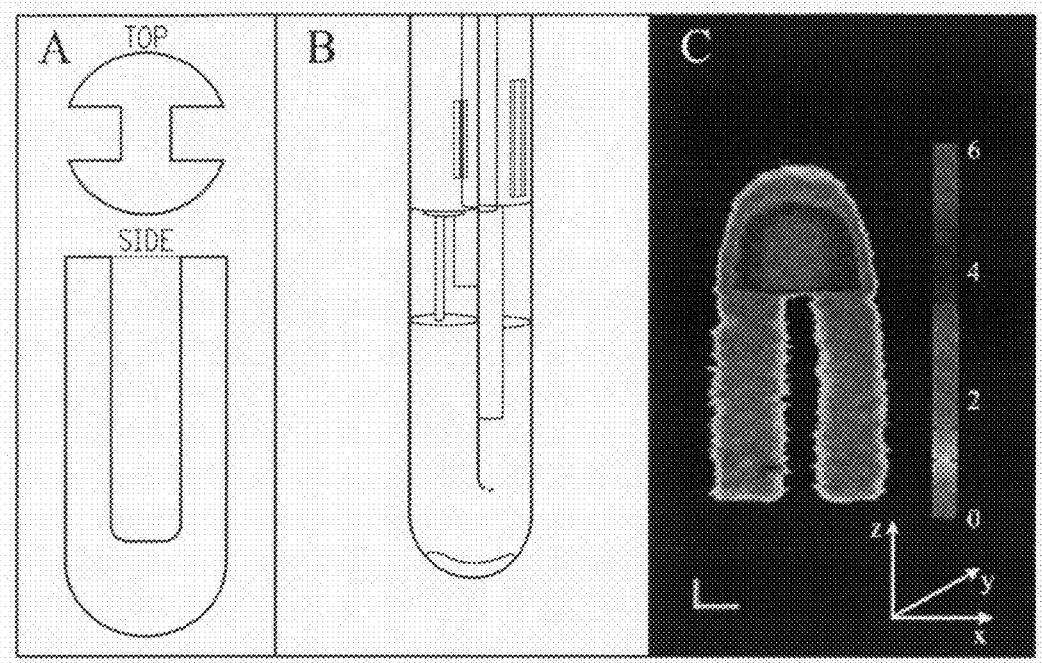
FIG. 4 shows (A) top and side of a sample vessel used in this invention for contrast flow imaging, (B) a photograph of the sample vessel, and (C) a static MRI of the sample vessel.
Figure 5:
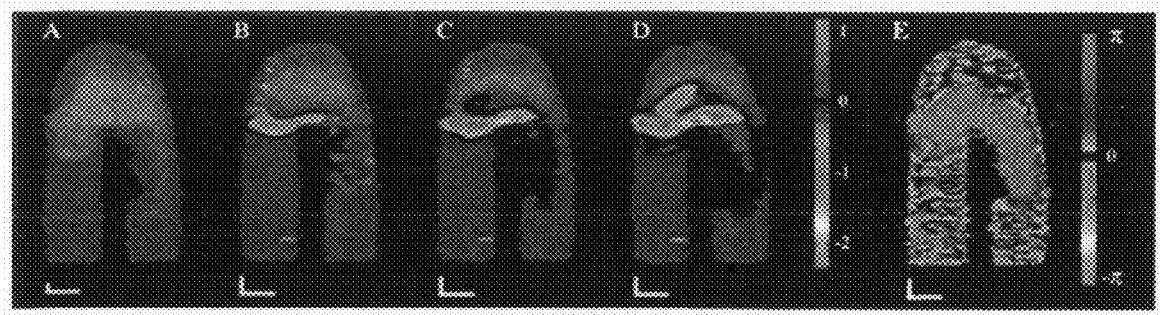
FIG. 5 shows (A) a contrast flow image using $^1$H hyperpolarized water in the sample vessel of FIGS. 3A-C, under continuous water flow without microwave irradiation, (B) a contrast flow image using $^1$H hyper-polarized water in the sample vessel of FIGS. 3A-C, under a water flow rate of 0.5 ml/minute using strong microwave irradiation, (C) a contrast flow image using $^1$H hyper-polarized water in the sample vessel of FIGS. 3A-C, under a water flow rate of 1 ml/minute using strong microwave irradiation, (D) a contrast flow image using $^1$H hyper-polarized water in the sample vessel of FIGS. 3A-C, under a water flow rate of 1.5 ml/minute using strong microwave irradiation, and (E) a phase map distinctively showing the flow path of negatively enhanced hyper-polarized water in the sample vessel of FIGS. 3A-C.

After we have successfully demonstrated our capability to control contrast using NMR spectroscopy, we pursued MRI experiments for the visualization of the flow path through model samples. We chose a simple reactor vessel to test our setup and contrast imaging methodology, described as follows. A phantom was created from a cylindrical glass tube (ID=4 mm) with a PTFE plug constraining the water volume in a characteristic fashion (FIG. 4A) with a cylindrical reservoir in the upper part connected to two parallel channels below, as can be seen in the photograph (FIG. 4B) and 2D NMR spin-warp image (FIG. 4C) obtained along the x and z directions with proper sample orientation. The stronger signal intensity of the upper water reservoir reflects the larger water volume as the 2D image is a projection along the y direction, and the rounded shape of the upper part of the image is due to severe field inhomogeneity in this region of the electromagnet. Also depicted in the photo are the inlet and outlet capillaries (ID=700 μm) for water flow, where the longer capillary sticking into the channel was the outlet for the image experiments presented in FIG. 4B. Flowing water (between 0.5-1.5 ml/min) shows slightly higher intensity (FIG. 5A) than static water as it carries polarization that is less depleted by radio frequency pulses, which is due to the repetition delay being shorter than the $^1$H spin relaxation time back to equilibrium (less than the ideal waiting time of $5 \cdot T_1 = 13.5$ s was employed due to flow volume, i.e. time, restriction of our syringe pump). This circumstance leads to a $T_1$ weighted contrast in FIG. 5A where the pathway of the water entering the upper reservoir, reaching into the channel on the right hand side and back out is indirectly visualized.

Visualization of Flow Pattern Through a Water-Filled Model Reactor Vessel

While water is flowing, the microwave irradiation is turned on and the cavity tuned on-resonance to the ESR frequency of the center line of the nitroxide signal, which leads to partial ESR saturation and therefore amplifies the $^1$H signal of flowing water. Note that the signal of the hyperpolarized water as it exits the microwave cavity is inverted, as mentioned above, and also when the spins reach the sample faster within the given $T_1$ relaxation time scale of radical-free water (~2.7 s) that greater amplification is observed with increasing flow rates (increasing from 0.5-1.5 ml/min in FIG. 5B to 5D). This results in a large negative signal at the inlet side of the contrast images. As time progresses the NMR signal of the water decays exponentially towards the equilibrium value. We can therefore track the flow of water by observing the gradually decaying negative signal as it leaves the inlet capillary (left hand side of images in FIGS. 5B-D), travels across the upper reservoir, enters the narrow channel and finally is forced out towards the exit capillary (right hand side of the images). The fast flow entering the vessel and bouncing off the PTFE phantom leads to vortex-like structures, which become distinct at higher flow rates (FIG. 5D).

Figure 6:
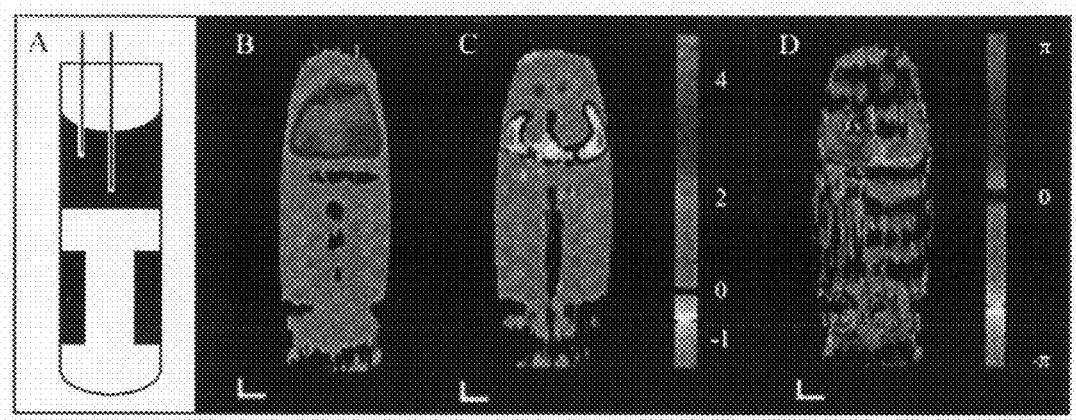
FIG. 6 shows (A) another schematic depiction of a sample vessel used in this invention, (B) a contrast flow image using $^1$H hyper-polarized water in the sample vessel of FIG. 5A, under continuous water flow without microwave irradiation, (C) a contrast flow image using $^1$H hyper-polarized water in the sample vessel of FIG. 5A, under a water flow rate of 1.5 ml/minute using strong microwave irradiation, and (D) a phase map distinctively showing the flow path of negatively enhanced hyper-polarized water in the sample vessel of FIG. 5A.

This "bouncing" effect led to the observation of a circular vortex pattern (FIGS. 6B-D) in a vessel where no channels were connected to the upper reservoir into which the flowing water can escape (FIG. 6A). The water's flow can be visualized as entering through the capillary, bouncing off the bottom of the vessel, splitting in two directions, and then turning around and flowing out of the vessel. Such flow patterns are very difficult to experimentally observe without the use of exogenous contrast agents (e.g. dye molecules), which chemicals may change the flow property and are not desirable for biological samples.

Slower flow rates provide a more accurate picture of the flow dispersion near the inlet capillary because at higher flow rates the distance traveled during the echo- and acquisition time of the image pulse sequence falsifies the intensity distribution. This explains the shift of the most intense signal region by about 1-2 mm further away from the tip of the inlet capillary at higher flow rates.

Figure 7:
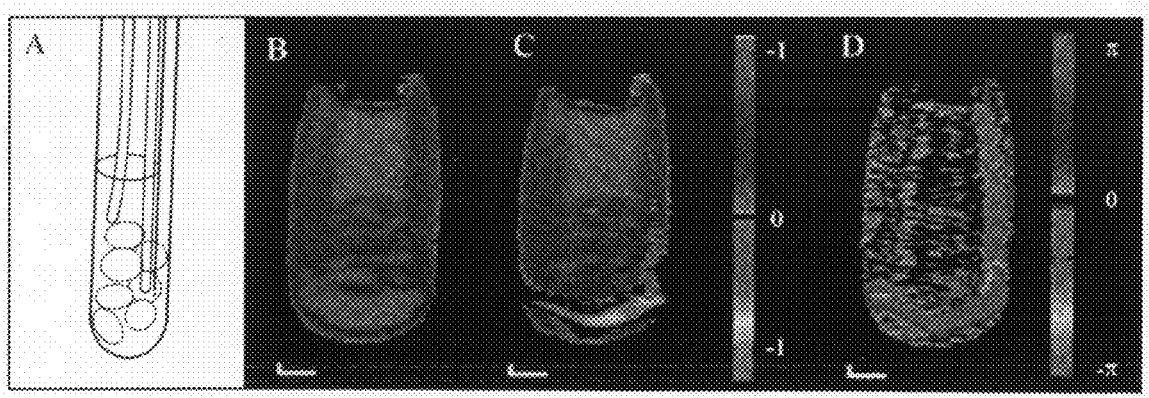
FIG. 7 shows (A) a photograph of a sample vessel containing water-saturated molecular sieve beads, (B) a contrast flow image using $^1$H hyper-polarized water in the sample vessel of FIG. 6A, under continuous water flow without microwave irradiation, (C) a contrast flow image using $^1$H hyper-polarized water in the sample vessel of FIG. 6A, under a water flow rate of 1.5 ml/minute using strong microwave irradiation, and (D) a phase map distinctively showing the flow path of negatively hyper-polarized water around the large beads.

The voxels originating from inverted polarization contain 180-degree phase shifted NMR signal when detected as transverse magnetization. In other words, a $\pi/2$ pulse with a given phase information, say x, will turn positive polarization (thermally polarized nuclei) into transverse magnetization along they axis and negative polarization (DNP polarized nuclei) along the -y axis. This phase shift of $\pi$ is displayed in a phase map (FIGS. 5E, 6D and 7D), which shows the spatial occupation of the negatively polarized water as it enters the cell (FIG. 5E is obtained from FIG. 5D using FIG. 5A as a reference, and FIG. 6D is obtained from FIG. 6C using FIG. 6B as a reference, etc.).

Visualization of Flow Dispersion Through Water-Saturated Molecular Sieve Packing Another model system that we have studied is the flow of water into a packing of 8-10 mesh molecular sieves, where more geometrical hindrance and therefore greater mechanical flow dispersion exists (FIG. 7A), demonstrating the utility of our novel contrast methodology for flow through restricted and complex media including separation columns, reactors packed with solid catalyst or biological tissues. The first image, acquired while flowing and without applying microwave (FIG. 7B), depicts density contrast where the $^1$H image intensity is reduced due to the presence of molecular sieves. Also, one notices an air bubble trapped just to the left of the inlet tip where the signal intensity is reduced as well. When the microwave, and therefore the contrast, is turned on, we again see inverted signal at the inlet capillary (the one that reaches deeper into the sample at the right hand side of the sample as can be seen in FIG. 7A). The decay of the signal clearly shows the path of the water out of the inlet capillary along the bottom of the tube around the beads towards the outlet capillary (FIG. 7C). The phase map further confirms the pathway of the inflowing hyper-polarized water by means of phase values of $+/-\pi$ that visualizes the trajectory of the negatively polarized water (FIG. 7D). The further recovery through zero back to positively polarized equilibrium value cannot be seen in the phase map because the phase between returning and equilibrium polarization is the same. This pattern is confirmed by comparing the coinciding zero intensity around the contrasted region of FIG. 7C.

Relationship to Other DNP Efforts

The direct enhancement of fluids through DNP by up to two orders of magnitude has been known for decades [4, 9, 10]. DNP has reached prominence through the recent enhancement by the Golman group of $^1$H, $^{13}$C and $^{15}$N by up to four orders of magnitude at 1.2K [11]. The main obstacles remaining, in order to utilize this extremely high DNP polarization for sensitive high-resolution NMR spectroscopy, consist of quickly elevating the frozen matrix to ambient temperatures and efficiently eliminating radicals prior to detection. The Golman group successfully preserved much of the polarization by quickly dissolving polarized solids in hot water and filtering out the radicals through an ion-exchange column [11]. The polarization matrix presented here may be superior for such applications because the polarized fluid only needs to be separated from the gel matrix after DNP. This method is not only technically simpler and quicker for radical elimination, but does not leave radical residues in the effluent that are detectable by ESR. Additionally, the polarization matrix of the present invention may be more compatible with biological samples because ion exchange matrices nonspecifically remove all positively or negatively charged molecules and looses its binding efficiency under high salt conditions.

Applicability of the Methodology

A novel methodology has been presented here to selectively and significantly enhance the $^1$H NMR signal of the injected water so that it manifests distinct contrast from the NMR signal of the bulk water. Flow traces were successfully visualized with unique and distinct contrast on model systems. This suggests a novel tool for flow tracking in model reactors and separation columns. Furthermore, this methodology is readily adaptable to blood and tissue perfusion MRI in vivo. As MRI normally utilizes the abundant $^1$H signal of water, the main limitation is not the low signal-to-noise ratio, but the low contrast-to-noise ratio in accurately tracking blood flow or visualizing, e.g., poorly perfused tissue regions as may be the case with tumors. Using the methodology of the present invention, the ex vivo production of hyperpolarized infusion fluids as well as their in vivo injection for subsequent MRI scanning can take place within the same magnetic field, where the DNP process can take place at a much less homogeneous region of the magnet compared to MRI. The DNP polarization efficiency as well as imaging quality of susceptibility broadened heterogeneous tissues is high at 0.35 T, while at 1.5 T field, the DNP efficiency is reduced by a factor of ~4-5, but a higher signal-to-noise ratio and resolution for imaging is expected.

Comparison to a Related Overhauser-Enhanced Contrast MRI Technique: PEDRI

Another in vivo imaging technique for fluid tracking is dubbed PEDRI (proton electron double resonance imaging), which relies on in vivo injection of stable radicals and direct DNP polarization of adjacent $^1$H inside the living subject at ultra low fields of 0.01-0.02 T [12, 13]. With this method, localized contrast and longer observation times can be achieved. However, there is a toxicity concern regarding the radicals, the origin of the contrast is indirect as it is given through the pathway of the stable radical and not the polarized molecule, and the experiment must operate at extremely low magnetic field, compromising the detection sensitivity and image resolution.

Observation Time Given by Hyper-Polarized $^1$H-Water Based Contrast Agents

The limited observation time (given by $T_1$), is less severe than it seems because high polarization can be achieved. Saline solution ($T_1 \sim 1.5$ s) with $-100$ fold hyper-polarization will provide distinct contrast during an observation time up to ~7-9 s that originates from polarization that has decayed to zero (see distinct boundaries at zero polarization in the images and phase maps of FIGS. 5, 6, and 7), and higher image resolution and sensitivity given by the significantly higher signal amplitude at shorter observation times of ~3-4 s. Note that the current technique of non-invasive perfusion imaging named artery spin labeling relies on contrast originating from the inversion of $^1$H magnetization, thus $-1$ fold polarization, so to speak, at the most. An important parameter to carefully consider is the time scale of observation versus recirculation and tissue perfusion. The stated 7-9 s observation time is longer than the ~4-5 s complete recirculation time of a mouse, and comparable to the perfusion time from human veins to central organs and the brain vasculature. Therefore, in vivo perfusion studies in mouse models and human subjects in part are viable prospects of the presented methodology.

In summary, water itself in a highly spin-polarized state is introduced as a perfectly non-invasive and authentic contrast agent to visualize its characteristic flow pathway through porous samples in aqueous media and biological subjects in vivo. We demonstrated on three water-filled model reactor vessels that unique and distinct contrast visualizing the flow pathway, vortices and flow dispersion can be obtained. The applicability of this methodology for perfusion imaging in medical applications in a 0.3-1.5 Tesla MRI scanner is straightforward.

The effective polarization and production of radical-free water in the hyper-polarized state through the use of immobilized free TEMPO radical onto gel filtration chromatography materials is a key invention. Cross-linked sepharose is an ideal matrix for polarizing biological samples within because the disperse chains create large pores that allow water to flow through at an accelerated rate. Sepharose is biologically friendly due to its low affinity towards biomolecules, and therefore is commonly used in protein purification. The agarose chains of sepharose provide high mobility to the covalently attached radicals—a necessary requirement for the Overhauser effect because the energy for exchange interactions is obtained through translational motion. Another key advantage of this porous media is that the molecule to be polarized remains in contact with the radicals longer while it resides within the pores that facilitates high polarization, but follows the fast flow stream once it exits the pores.

Second Embodiment

We present in this embodiment a unique analysis tool for the selective detection of local water on the surface and inside soft molecular assemblies—hydrophobic cores, vesicular bilayers, and micellar structures, protein surfaces and complex coacervates—suspended in bulk water. Through the use of DNP, the $^1$H NMR signal of water is amplified as it interacts with stable radicals that possess ~658 times higher spin polarization. To exemplify the utility of this DNP method, we utilized stable nitroxide radicals covalently attached along the hydrophobic tail of stearic acid molecules that incorporate themselves into surfactant-based micelle or vesicle structures. Here we present a study of local water content and fluid viscosity inside oleate micelles and vesicles and Triton X-100 micelles to serve as model systems for soft molecular assemblies. This approach is unique because the amplification of NMR signal is performed in bulk solution and under ambient conditions with site-specific spin labels that only detect the water that is directly interacting with the localized spin labels. Continuous wave (cw) ESR analysis provides rotational dynamics of the spin-labeled molecular chain segments and local polarity parameters that can be related to hydration properties, whereas we show that DNP-enhanced $^1$H NMR analysis of fluid samples directly provides translational water dynamics, i.e. fluid viscosity, of the local environment probed by the spin label.

Our technique therefore provides a powerful analysis tool, complementary to cw ESR, to study hydration characteristics of surfactant assemblies, lipid bilayers or protein aggregates, where water dynamics is a key parameter of their structure and function. Furthermore, real-time monitoring of dynamic events that accompany water exclusion or hydration as key characteristics, such as the aggregation of tau or Aβ-proteins—concurring in many neurodegenerative diseases including Alzheimer disease—or the degradation and molecule release of soft matter assembly-based drug delivery systems, become possible. The nature of protein aggregation intermediates are thought to be key toxic species, which nature can only be fully elucidated if combined with dynamic studies in situ. An important aspect is that our X-band DNP tool can be easily implemented by any interested researcher who has access to a standard cw ESR spectrometer and a single NMR channel at ~15 MHz frequencies.

Our aim, however, is not to maximize the NMR sensitivity by achieving large signal amplification factors, but to create significant and meaningful contrast from the background signal. This is realized using stable nitroxide spin labels covalently attached to surfactant molecules at specific positions to amplify only the $^1$H NMR signatures of the local environment, which represents the localized interactions between these spin labels and the solvent water.

Our DNP analysis tool relies on the widely known and studied Overhauser effect, which provides considerable amplification of $^1$H NMR signal of fluid water under ambient conditions through dipolar interactions between a $^1$H nucleus and an unpaired electron [47-51]. Borah and Bryant [52] found dipolar relaxation is dominantly driven by translational motion of the interacting species for the particular system of ¹H nuclei of water interacting with stable nitroxide spin labels. This makes the DNP-amplified ¹H NMR signal of solution samples predominantly sensitive to the translational fluid dynamics of water directly interacting with the spin label. The sensitivity of the Overhauser effect to diffusion has already been employed as a contrast mechanism to monitor gel formation [0054]. However there, the DNP effect was neither fully quantified in terms of motional parameters, nor employed in combination with ESR techniques by using site-specific spin labels to obtain localized molecular information and solvent dynamics. In this manner, DNP-amplified NMR analysis using spin labels is complementary to ESR line shape analysis of those spin labels, which directly provides the rotational (or some translational) diffusion rates of the spin-labeled molecular segment. We presented in recent work a refined theoretical model which fully describes all DNP parameters when the Overhauser mechanism is employed for solution-state molecules and stable nitroxide radicals [57], allowing for the explicit correlation between DNP contrast and fluid viscosity Referring to FIG. 8, a schematic sketch of a few examples of hydrated materials, where nitroxide spin labels (see schematic stick-figure) can be attached, as described in the text, to specific sites on the surface and interior of a variety of molecules, molecular assemblies and soft materials. A particular strength of our DNP NMR approach as described in this invention is that large proteins, molecular assemblies or cells, that are conventionally difficult to study by NMR because of signal overlap and large background signal, can be readily studied by our DNP NMR approach. We can utilize site directed mutagenesis of proteins and spin labeling of cystein aminoacids or use spin labels that are covalently functionalized on specific lipid or surfactant molecular positions, which monomers can be incorporated into molecular assemblies, such as micelles, vesicles or lipid membranes. This technique is extensively used in electron spin resonance spectroscopy. However, it is novel to employ dynamic nuclear polarization using this specifically spin labeled molecules to study the local water dynamics at the specific molecular site of interest on the surface and interior of hydrated materials. This figure, for example, illustrates a few hydrated materials that can be studied by our DNP NMR approach, but our invention is not limited to the application of these materials. The attachment of spin labels to specific molecular sites is illustrated by stick-and-a-dot probes incorporated into these hydrated materials. The first panel illustrates that proteins in solution as well as membrane proteins embedded in lipid and surfactant materials can be studied. The second panel in the first row shows that protein aggregation—a hallmark of many neurodegenerative diseases—can be studied at the early stage of aggregation and assembly. The second row illustrates that micelles, vesicles as well as planar bilayers composed of lipid or surfactant molecules can be studied by DNP NMR upon incorporation of spin labeled lipid or surfactant molecules into the assembly.

Our analysis tool was applied to Triton X-100 (8-carbon alkyl-phenol polyoxyethylene) and oleate (18-carbon fatty acid surfactant) micelle-vesicle model systems. Oleate is dispersed in aqueous solution when its concentration is below the critical micelle concentration (cmc) of oleate (0.7-1.4 mM), but will form micelles above the cmc and undergo a reversible micelle to vesicle transformation as the surfactant concentration of oleic acid matches that of oleate at lower pH [46, 58, 59]. We used oxazolidine-N-oxyl (doxyl) radicals as spin probes linked to the 16- and 5-carbon position of stearic acid surfactants (16-DS and 5-DS), which incorporate well into oleate micelle or vesicle assemblies[46]. Using DNP, ESR, and NMR relaxation measurements as complementary techniques, we characterized the role of fluid water in oleate and Triton X-100 molecular assemblies under ambient conditions through its interaction with spin labels.

Theoretical Basis

A theoretical understanding of the DNP mechanism is important for quantitative applications of this principle. We briefly describe here the basic principles relevant to the interpretation of our data.

The coupling factor, $\rho$, defined in Eq. 2 can be written in terms of the spectral density functions [49]:

$$\rho = \frac{6J(\omega_S + \omega_I, \tau) - J(\omega_S - \omega_I, \tau)}{6J(\omega_I + \omega_S, \tau) + 3J(\omega_I, \tau) + J(\omega_S - \omega_I, \tau)} \quad (5)$$

where the spectral density function $J(\omega)$ is given by (Hodges et al, Biophys J, 1997, 73, 2575-2579)

$$J(\omega, \tau) = \frac{1 + \frac{5\sqrt{2}}{8}(\omega\tau)^{1/2} + \frac{\omega\tau}{4}}{1 + (2\omega\tau)^{1/2} + (2\omega\tau) + \frac{\sqrt{2}}{3}(\omega\tau)^{3/2} + \frac{16}{81}(\omega\tau)^2 + \frac{4\sqrt{2}}{81}(\omega\tau)^{5/2} + \frac{(\omega\tau)^3}{81}} \quad (6)$$

Figure 9:
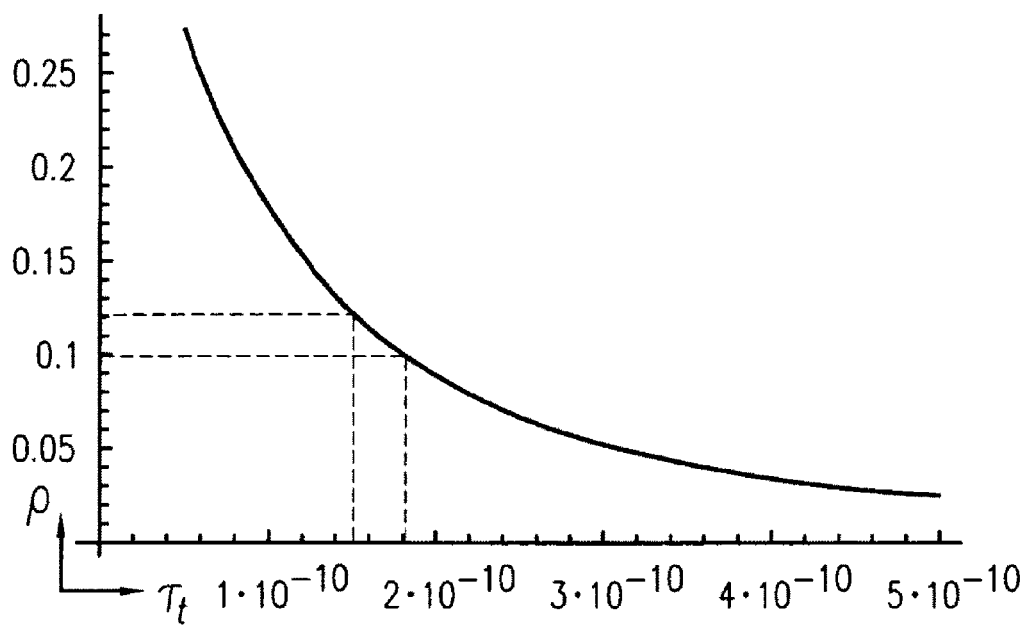
FIG. 9 is a plot showing that the coupling factor decreases as the translational correlation time increases following a characteristic relationship determined by the spin dynamics between nitroxide spin labels and water, as described in this invention.

By determining $\rho$ in a DNP experiment, Eq. 6 can then be used together with Eq. 5 to find the translational correlation time, $\tau$, which is a function of the diffusion coefficients of the two spin species following Eq. 7:

$$\tau = \frac{d^2}{D_I + D_S}, \quad (7)$$

where d is the distance of closest approach between the two spins and $D_I$ and $D_S$ are the diffusion coefficients of the solvent water and spin label respectively. For spin labeled molecules, $D_S$ is $<<D_I$ so knowledge of r gives direct information on the diffusion of local solvent water dynamics. FIG. 9, is a plot comparing the coupling factor and the translational correlation time ($\tau_t$ in FIG. 9 is same as $\tau$ in text). For a nitroxide radical in water, we measured $\tau$ be 76 ps, which numbers corresponds to a coupling factor of about 0.22. As $\tau$ increases, $\rho$ decreases in a characteristic fashion given by equations 5 and 6, and depicted in FIG. 9.

Figure 10:
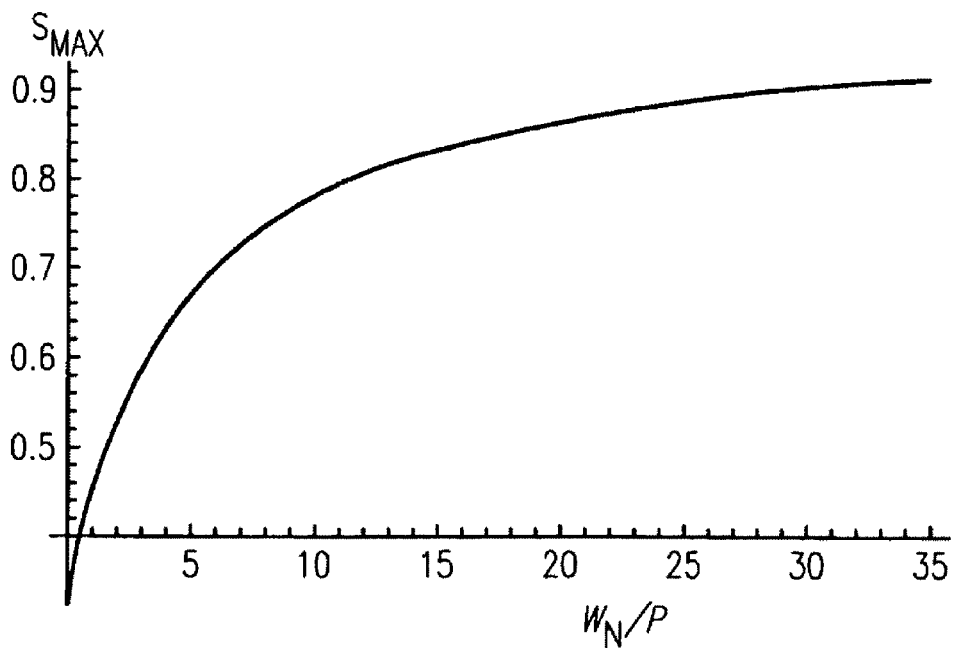
FIG. 10 is a plot of the maximum saturation factor, $s_{max}$, as a function of $w_N/p$ (nitrogen nuclear spin relaxation rate over electron spin relaxation rate).

The saturation factor (Eq. 4), s, for nitroxide radicals possessing three hyperfine states (due to the ¹⁴N having a nuclear spin I=1 interacting with the unpaired electron) depends on the $B_1$ amplitude for ESR irradiation and the efficiency with which the hyperfine states mix [57, 60]. We can extrapolate to infinite $B_1$ strength by measuring DNP enhancement at a series of $B_1$ amplitudes, thus eliminating $B_1$ strength variations at the sample as a variable. As has been discussed in detail elsewhere [57], the efficiency of mixing depends on the amplitude of intermolecular Heisenberg electron spin exchange and the nitroxide's nitrogen nuclear spin relaxation rate. The spin exchange effects can be neglected if intermolecular collision between the spin labels is hindered, e.g., due to low spin label concentration or if there is little chance for mutual interaction between the spin labels because only 1-2 of them are incorporated into isolated assemblies. However, it also has been shown that the nitroxide's nitrogen nuclear spin $T_1$ relaxation rate can be very high depending on the spin label's rotational motion [61], and thus can lead to efficient mixing of the hyperfine states [57]. Therefore, even in the absence of Heisenberg spin exchange effects between the three hyperfine lines of the spin labels, the saturation factor at infinite microwave power, $s_{max}$, can approach 1 as seen by equation 8.

$$s_{max} = \frac{1}{3}\left[\frac{(2+w_N/p+6^{\kappa'C}/p)(2+3^{w_N}/p+6^{\kappa'C}/p)}{4+(w_N/p+2^{\kappa'C}/p)(w_N/p+6^{\kappa'C}/p)+2(3^{w_N}/p+8^{\kappa'C}/p)}\right] \quad (8)$$

where $w_N$ is the nitrogen nuclear spin relaxation rate, p is the electron spin relaxation rate, $\kappa'$ is the electron spin exchange rate and C is the free radical concentration. A plot of $s_{max}$ vs. $w_N/p$ is shown in FIG. 10. If the spin labels experience rotational dynamics with correlation times ($\tau_{rot}$) between $7 \cdot 10^{-10}$ s–$5 \cdot 10^{-7}$ s, $w_N/p \geq 28$ and $s_{max}$ is ~1[61]. These correlation times cover the range of the relevant rotational diffusion rates ($R=1/6 \cdot \tau_{ro}$) that the spin labels incorporated in micelle or vesicle systems usually experience. As the nitroxide radicals are present in small concentrations and furthermore are incorporated into micelle or vesicle structures, they are well shielded from inter-radical collisions and Heisenberg exchange so $\kappa'=0$ to a very good approximation. However, note that non-negligible values of $\kappa>0$ would only strengthen the following argument.

The diffusion coefficient is related to the fluid viscosity ($\eta$) by the Stokes Einstein equation:

$$D = \frac{k_B T}{6\pi \eta r}. \quad (9)$$

Through this path we can compute the fluid viscosity ($\eta$) from the translational correlation time. Thus, fluid dynamics studies of soft matter applications as presented here, through the use of the DNP method, is well justified as a unique analysis tool complementary to NMR relaxometry and ESR.

Experimental Results

Figure 11:
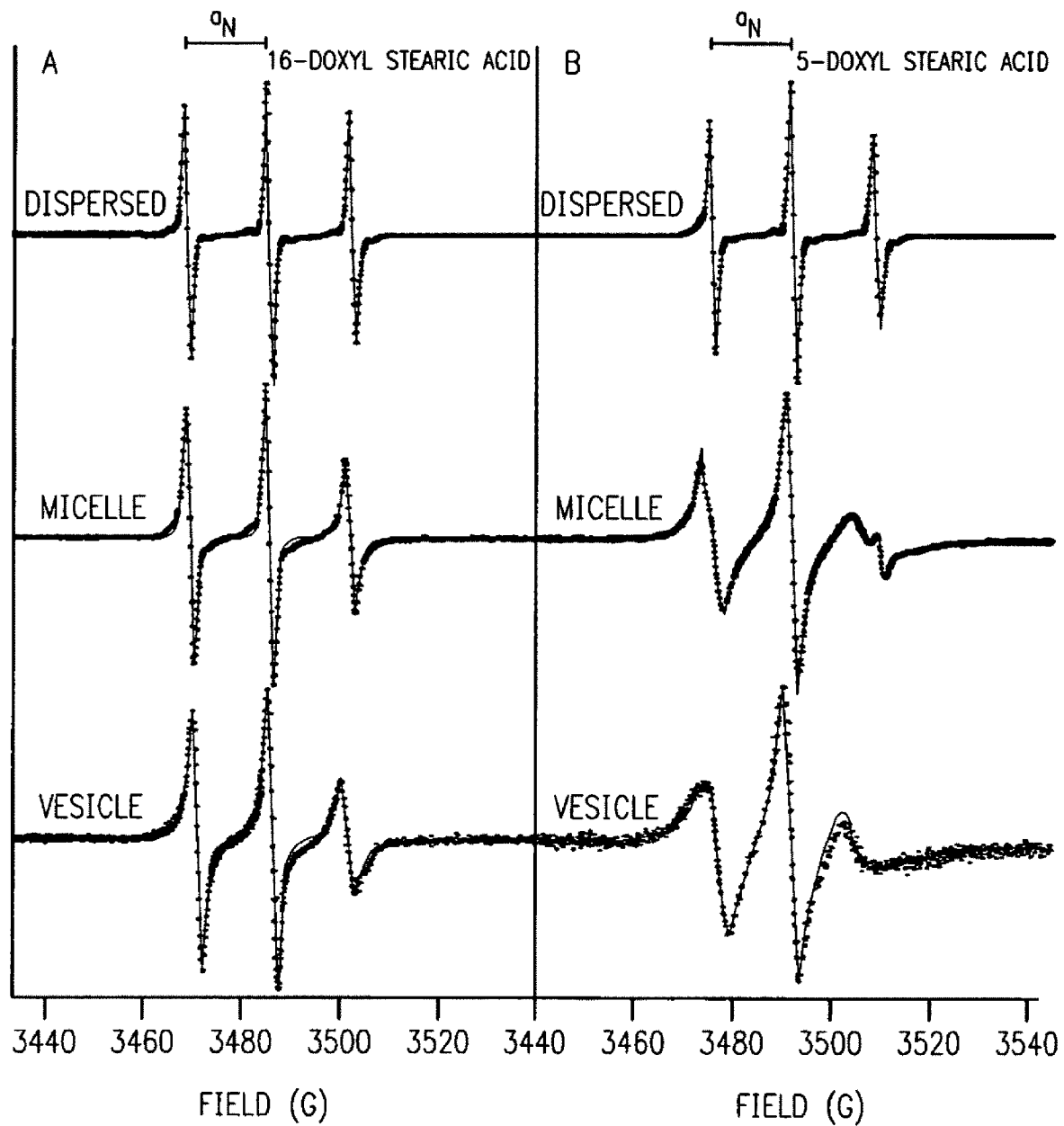
FIG. 11 is a plot showing continuous wave X-band ESR spectra of 16-DS (A) and 5-DS (B) spin probes as part of dispersed oleate surfactant solutions and incorporated into oleate micelle and vesicle assemblies in water at 295K (dotted spectra) overlaid with simulated and fitted spectra by the EasySpin program (straight line)

Samples. We prepared 300 µM of either 5-DS or 16-DS spin probes in both 200 µM (<<cmc) and 25 mM (>>cmc) oleate solutions. At 200 µM, the oleate surfactants are dispersed in solution, however, literature reports state that 5-DS has an extremely low cmc of ~35 µM [63], and therefore is not dispersed in solution under these experimental conditions. FIG. 11 is a plot of the continuous wave X-band ESR spectra of 16-DS (A) and 5-DS (B) spin probes as part of dispersed oleate surfactant solutions and incorporated into oleate micelle and vesicle assemblies in water at 295K (dotted spectra) overlaid with simulated and fit spectra by the EasySpin program (straight line). Rotational correlation times of both spin labeled probes and the hyperfine coupling tensor element $A_{zz}$ were obtained from the ESR spectral analysis. For the samples measured with 16-DS probes, the hyperfine coupling constant, $a_N$, was also obtained. The low cmc and the motionally narrowed ESR spectra for both 16-DS and 5-DS (FIG. 11, top row) together with other peculiar observations that we will report on later suggest that 5-DS or 16-DS form micelles in the presence of low concentration (200 µM) oleate surfactants, and rapidly exchange in and out of these assemblies.

At oleate concentrations of 25 mM and above pH=10.5, the surfactants as well as the 16-DS spin probes are completely incorporated into oleate micelles. The current understanding about oleate micelle dynamics is that the transition of free surfactant into micelle is significantly faster (correlation times<$10^{-9}$ s)[33] compared to the transition of micelle to monomeric surfactants (>$10^{-4}$ s) [64], which means that we can safely assume that the spin labeled surfactants are probing the micelle volume and not an average property between monomeric surfactant solution and the micelle interior. The fast surfactant diffusion from water into micelle also implies that the water exchange in and out of the micelles is significantly faster, with lipid-water association lifetime of the order of <100 ps [17, 25]. When using 5-DS, a small fraction of residual spin probes fail to incorporate into the micelles (an extra signature appears in the ESR spectrum of the micelle sample, see FIG. 11B, middle). In addition to literature precedence stating the presence and localization of the spin label radicals in the core of the oleate micelles [46, 65], we confirmed the incorporation of 16- and 5-DS through paramagnetic $T_2$ relaxation enhanced (PRE) NMR analysis (data not shown) and the observation of completely (16-DS) or mostly (5-DS) homogeneous ESR populations.

Purely micellar structures (rod like, Ø~4.5 nm) [59, 66] are formed above pH 10.5, a mixture of micelles and vesicles are formed between pH 10.5 and 8, and predominately vesicular oleate structures (Ø~140 nm) [59] found below pH 8. A solution of 300 µM 16-DS in 100 mM Triton X-100 was prepared to probe Triton X-100 micelles (spherical shape, Ø~3 nm, cmc=0.2 mM) [66]. Measurements of $^1$H NMR $T_1$ and $T_2$ relaxation, cw ESR of the spin probes, and $^1$H DNP characterization of local water were carried out in the presence of 5-DS or 16-DS spin probes in surfactant solutions under conditions where the probes are dispersed in solution or incorporated into micelles and/or vesicles samples.

$^1$H $T_1$ NMR relaxation measurements of spin probes. $T_1$ relaxation times of the $^1$H NMR signal of water in the presence and absence of spin probes incorporated in micelle, vesicle and mixed assemblies were measured, and the leakage factor (Eq. 3) computed, as listed in Table. 1. One notices that f is approximately equal between the two spin probes (300 µM concentration of 5-DS or 16-DS) in micelle or vesicle systems (and also in dispersed oleate surfactants; data not shown). An important observation is that even though the probes have close to the same leakage factor, f shows small variations between the different samples of oleate micelles (f~0.11), micelle/vesicle mixed as well as predominant vesicle phase (f~0.13: samples 3-5, 7-8 in Tab. 1), oleate vesicular aggregates (f~0.22) and Triton X-100 micelles (f~0.17), probed by 16-DS spin probes.

TABLE 1

| Sample | pH | F | $E_{max}$ | $\rho \cdot s_{max}$ |
| --- | --- | --- | --- | --- |
| 1) 5-DS micelle | 11.1 | 0.103 (8) | −6.9 (5) | 0.12 (1) |
| 2) 16-DS micelle | 11.2 | 0.111 (8) | −6.3 (7) | 0.10 (1) |
| 3) 16-DS mixed | 10.0 | 0.134 (9) | −4.3 (4) | 0.060 (6) |
| 4) 16-DS mixed | 9.2 | 0.134 (9) | −1.4 (5) | 0.027 (6) |
| 5) 16-DS mixed | 9.0 | 0.14 (1) | −1.5 (2) | 0.027 (3) |
| 6) 5-DS vesicle | 8.6 | 0.13 (2) | −2.0 (4) | 0.035 (3) |
| 7) 16-DS vesicle | 8.6 | 0.121 (8) | −1.1 (2) | 0.026 (3) |
| 8) 16-DS vesicle | 8.2 | 0.130 (9) | −1.0 (2) | 0.023 (3) |
| 9) 5-DS aggregate | 7.3 | 0.25 (2) | −1.4 (1) | 0.015 (1) |
| 10) 16-DS aggregate | 7.3 | 0.22 (2) | −0.6 (3) | 0.011 (2) |

Continuous wave ESR characterization of spin probes in oleate assemblies. ESR spectra of nitroxide spin labels inherit spectral features from the anisotropic rotational characteristics of the spin probes. Modeling programs based on the stochastic-Liouville equation [67] can be used to estimate axial rotational rates of the spin labeled molecular segments in micelle and vesicle structures. Programs in the literature include the nonlinear least-squares (NLSL) ESR spectra fitting program [68] and the simulation and fitting program package (EasySpin, ETH [69]). We employed the EasySpin program to obtain rotational correlation times for the 5- and 16-doxyl stearic acid probes using g and A tensor elements of $g_{xx}=2.0088$, $g_{yy}=2.0061$, $g_{zz}=2.0027$, $A_{xx}=6.26$ G, $A_{yy}=5.85$ G, and $A_{zz}=31.9$ G to 35.4 G depending on the sample (the differing hyperfine coupling constants will be discussed later). A diffusion tilt angle between 39-40 degrees and a basis set of truncation values of $L_{max}^{e}=24$, $L_{max}^{o}=14$, $K_{max}=6$, $K_{min}=6$ were used in the simulation [38, 70]. An isotropic rotation model in the fast rotation limit was employed for the samples with surfactants dispersed in solution and spin probes showing high motional freedom (Easy spin function, garlic). For the samples with the spin labeled surfactant probes incorporated into micelles or vesicles, a model using a slow rotation model was employed, where axial rotation of the probe was assumed to yield perpendicular ($R_\perp$) and parallel ($R_\parallel$) rotational diffusion rates relative to the long axis of the probe (Easy spin function, chili). Each spectrum was fit using the Easy Spin esfit function, while letting the rotation rates ($R_\perp$, $R_\parallel$) and $A_{zz}$ vary. Due to the presence of a small second population of the 5-DS in oleate micelle samples, this spectrum was simulated manually by adding two simulated spectra to produce a "fit spectrum". Then, the chi-squared value between the combined simulation and the experimental data was iteratively minimized over consecutive runs, while visually monitoring the shape of the simulation with respect to the experimental data. The simulated fits, axial rotational diffusion rates, and $A_{zz}$ values are presented in FIG. 11 and table 2.

The ESR spectrum of 16-DS (FIG. 11A, bottom; $R_\perp=0.87\times10^8$, $R_\parallel=8.53\times10^8$) and 5-DS (FIG. 11B, bottom; $R_\perp=0.26\times10^8$, $R_\parallel=2.62\times10^8$) incorporated into vesicle structures (25 mM oleate at pH<8) both reveal a relatively small (1-3 fold for $R_\parallel$ and $R_\perp$) decrease in rotational diffusion rates compared to those in micelle structures. An interesting feature to note is that there is an increase in the ratio between $R_\parallel$ and $R_\perp$ for 16-DS as well as 5-DS from ~7 in oleate micelles to ~10 in oleate vesicles, which indicates an increase of surfactant order in the vesicle's bilayer compared to the micelle core (Table 2).

Figure 12:
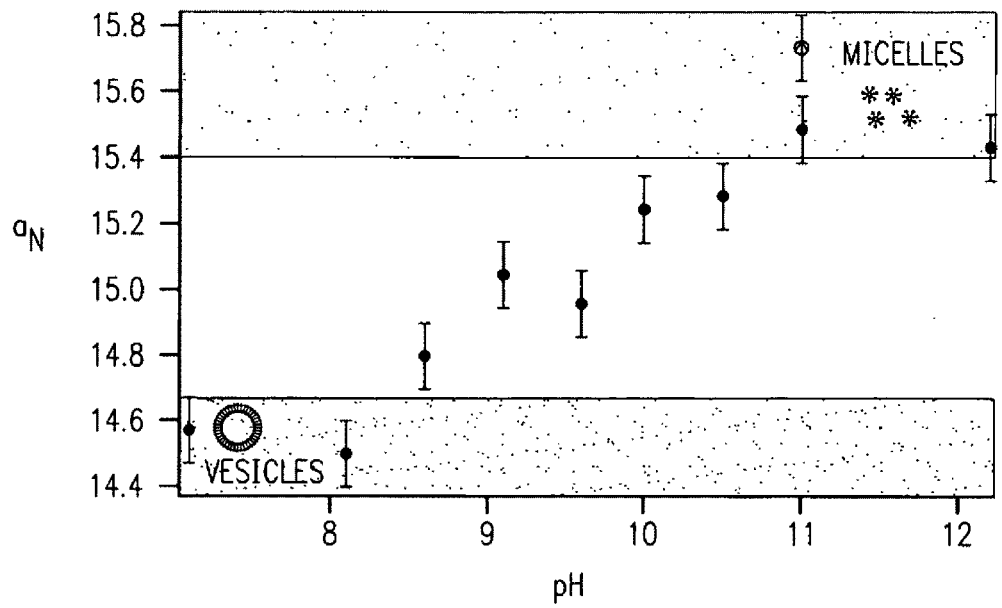
FIG. 12 is a plot showing the hyperfine coupling constant, $a_N$, measured by the extent of hyperfine splitting in the cw ESR spectra of 16-DS and 5-DS spin labeled oleate, displayed as a function of pH.

Besides rotational diffusion, the hyperfine coupling constants, $a_N$, that measure the hyperfine splitting of the unpaired electron due to the nitroxide's $^{14}N$ nuclear spin were obtained from the cw ESR spectra of 16-DS. FIG. 12 is a plot showing the hyperfine coupling constant, $a_N$, measured by the extent of hyperfine splitting in the cw ESR spectra of the nitroxide based spin probes, displayed as a function of pH. Above pH 10, most surfactants are included in micelles, and below pH 8 in vesicles, while in the intermediate pH range micelles and vesicles are in mixed in equilibrium. Because the measurement of $a_N$ is difficult for broad ESR spectra that show considerable rotational anisotropy and inhomogeneous broadening, we only obtained $a_N$ of 16-DS spin probes that display smaller rotational anisotropy. The hyperfine coupling constant, $a_N$, gradually decreases with increasing vesicle fraction, from a pure oleate micelle solution ($a_N=15.49$ at pH=11), to a mixture of micelle and vesicles, to a pure oleate vesicular solution ($a_N=14.57$ pH=7.1), in agreement with previously reported data [46].

TABLE 2

| | 5-Doxyl Stearic Acid | | | 16-Doxyl Stearic Acid | | |
|---|---|---|---|---|---|---|
| | $A_{zz}$ (G) | $R_\perp$ (s$^{-1}$) | $R_\parallel$ (s$^{-1}$) | $A_{zz}$ (G) | $R_\perp$ (s$^{-1}$) | $R_\parallel$ (s$^{-1}$) |
| Dispersed Oleate | 35.3 | $R_{iso}=7.50\times10^8$ | | 35.4 | $R_{iso}=10.0\times10^8$ | |
| Oleate Micelles | 34.3 | $0.47\times10^8$ | $3.30\times10^8$ | 34.3 | $2.58\times10^8$ | $19.5\times10^8$ |
| Oleate Vesicles | 34.2 | $0.26\times10^8$ | $2.62\times10^8$ | 31.7 | $0.87\times10^8$ | $8.53\times10^8$ |
| Triton X-100 Micelles | N/A | N/A | N/A | 31.6 | $0.75\times10^8$ | $9.57\times10^8$ |

The ESR spectra of 16-DS (FIG. 11A, top) and 5-DS (FIG. 11B, top) in dispersed surfactant solutions are similar, and show large, isotropic, rotational diffusion rates of $\sim 1\cdot 10^9$ s$^{-1}$ for both spin probes, indicating that both spin labeled surfactants display high rotational freedom independent of chain position. When the spin probes are incorporated into the oleate micelle solution, the ESR spectra broaden for both 16-DS (FIG. 11A, middle) and 5-DS (FIG. 11B, middle) due to motional restriction of the spin probe inside the micelle structure, which is more significant for $R_\perp$ than in $R_\parallel$, due to the axial rotation restriction. The alkyl chain of the spin label provides flexibility inside the micelles, yet still leads to strong anisotropic rotation (ratio of $R_\parallel$ to $R_\perp$ is ~7:1) in micelles. We see a much greater change between solution and micelle dynamics using the 5-DS ($R_\perp=0.47\times10^8$, $R_\parallel=3.30\times10^8$) as compared to the 16-DS ($R_\perp=2.58\times10^8$, $R_\parallel=19.50\times10^8$) spin labels. This is because, even though both probes are incorporated inside the same micelle core, 5-DS is situated closer towards the charged head of the stearate molecule, where it interacts with and is tethered by the relatively rigid interfacial layer. So, while the overall motion of the spin probes slows down due to an increase in local fluid viscosity in the more crowded micelle core compared to bulk water, 5-DS is additionally restricted by its interaction with the micelle-solution interface.

Figure 13:
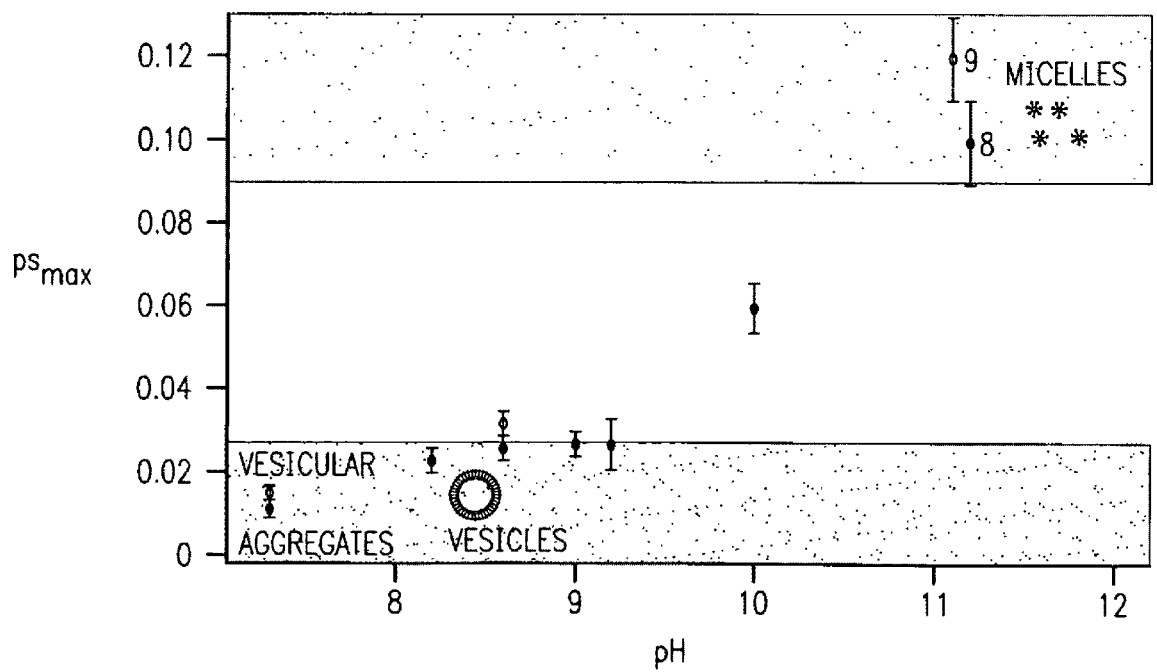
FIG. 13 is a plot showing ($E_{max}$), $\rho \cdot s_{max}$ calculated and displayed as a function of pH for 25 mM oleate solution with 300 uM spins, using the maximum DNP enhancement of $^1$H NMR signal. See table I for the characteristics of the specific samples plotted here.

$^1$H DNP characterization of local water in oleate assemblies. Subsequent to each cw ESR measurement, the $^1$H NMR DNP-enhancement of water was analyzed. Relevant to note here is that the $^1$H NMR detection coil is implemented inside the ESR cavity such that both ESR irradiation and NMR detection are permitted. Thus, we performed independent ESR and DNP measurements on the same samples using the same instrumental setup [62]. Referring to FIG. 13, the maximum DNP of $^1$H NMR signal ($E_{max}$) and leakage factor was measured, and from those values $\rho \cdot s_{max}$ determined for a pH range of 7-11 for 25 mM oleate assemblies containing 16-DS probes (Table 1; filled circles in FIG. 13) and for some 25 mM oleate assemblies probed by 5-DS (Table 1; open circles in FIG. 13). The $^1$H DNP enhancement factor $E_{max}$, and thus $\rho \cdot s_{max}$ of water inside the micelle volume was the highest ($\rho \cdot s_{max}$ around 0.1-0.12) in micelle solutions. When steadily increasing the vesicle fraction by gradually changing the pH from 12 to 7, the maximum DNP enhancement factor, and thus $\rho \cdot s_{max}$, gradually decreased until little DNP enhancement was observed in the vesicle solution ($\rho \cdot s_{max}$ around 0.011-0.015; see FIG. 13 and Table 1).

An important observation here is that the DNP induced $^1$H signal enhancement measured with the different spin probes, 5-DS and 16-DS, resulted in (within error) equal or very close DNP enhancements (and coupling factors) when incorporated into the same micelle or vesicle assemblies, even though the ESR rotational diffusion rates of 5-DS and 16-DS probes are markedly different. The rotational diffusion rates obtained from ESR measurements of 5-DS radical probes are vastly slower than 16-DS radical probes (~5 fold), as discussed above, although they are incorporated into the same micelle structures. This difference is greater than that between the rotational diffusion for 16-DS probes inside micelles versus vesicles (~2-3 fold). These observations confirm an important expectation that the $^1$H DNP enhancements are insensitive to the rotational diffusion dynamics of the spin probes (unlike ESR), but very sensitive to the content and translational diffusion dynamics of fluid water ($D_I$ in Eq. 7) inside the local soft structures.

Figure 14:
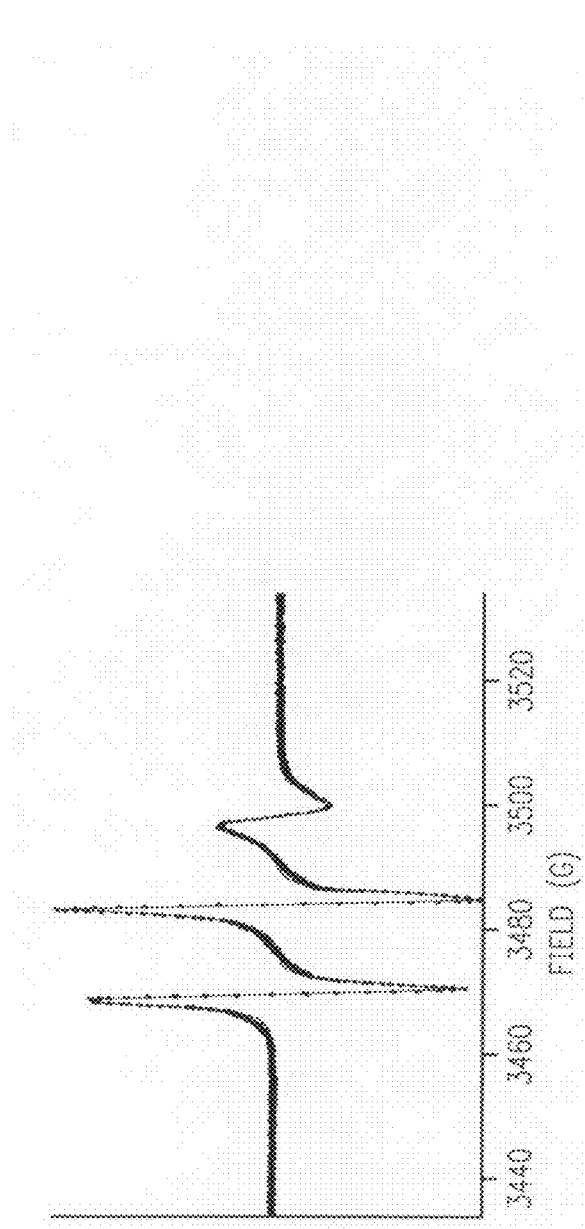
FIG. 14 is a plot showing continuous wave X-band ESR spectra of 16-DS spin probes incorporated into Triton X-100 micelles in water at 295K (dotted spectra) together with simulated and fitted spectra by the EasySpin program (straight line)

Continuous wave ESR and $^1$H DNP characterization of Triton X-100 micelles. To further verify that DNP is sensitive to water content in other localized environments, we studied the core of Triton X-100 micelles, and compared them to the results obtained from oleate micelles. Triton X-100 has been proposed to exclude water from the core of its micelles [71]. FIG. 14 is a continuous wave X-band ESR spectra of 16-DS spin probes incorporated into Triton X-100 micelles in water at 295K (dotted spectra) together with simulated and fitted spectra by the EasySpin program (straight line). Rotational correlation times of the spin labeled chain segment and the hyperfine coupling tensor element $A_{zz}$ were obtained from the ESR spectral analysis. The ESR spectrum of 300 µM 16-DS incorporated into 100 mM Triton X-100 micelles show broader features and slower diffusion rates ($R_\perp=0.75\times10^8$, $R_\parallel=9.57\times10^8$) compared to 16-DS incorporated in oleate micelles ($R_\perp=2.58\times10^8$, $R_\parallel=19.50\times10^8$; see FIG. 14, Table 2), which means that the spin label's mobility at the hydrophobic tail is reduced compared to oleate micelles, probably due to the much more compact size and packing of the Triton X-100 micelles. Furthermore, as expected, the $^1$H DNP measurements of 16-DS in Triton X-100 micelle solution show a drastically reduced enhancement of only −1 fold and $\rho \cdot s_{max}=0.018$ as opposed to $E_{max}=-6.3$ fold and $\rho \cdot s_{max}=0.10$ in oleate micelles (Table 1), which is attributed to significantly reduced water content within the Triton X-100 micelles. This observation is also in agreement with the measurement of a low hyperfine coupling constant for Triton X-100 micelles of $a_N=14.48$, which is a similar value as for 16-DS incorporated in hydrophobic vesicle bilayers.

DISCUSSION

The fluid water inside of micelle or vesicle assemblies is often difficult to discern from bulk water by conventional spectroscopic methods, motivating the development of new experimental methods to measure hydration and the dynamics of water inside fluid soft molecular assemblies. Our approach makes use of Overhauser-driven $^1$H DNP by employing nitroxide spin labels as reporter probes inside micelle and vesicle systems, with the spin labels localized at specific sites either inside the core, towards the interfacial layer, or in solution to determine local fluid dynamics. As discussed before we can easily measure f, and $s_{max}$ can be considered equal to 1 for micelle and vesicle solutions. Therefore, by measuring $E_{max}$ and f we can solve Eq. 1 for $\rho$. It is remarkable that the saturation factor of ESR resonances at maximum power, $s_{max}$, can be excluded as a dominant DNP variable for a large motional range covering three orders of magnitude ($\tau_{rot} \sim 7 \cdot 10^{-10}$ s-$5 \cdot 10^{-7}$ s), that includes the relevant slower rotational chain dynamics ($R_\perp$ in Table 2) inside micelles, fluidic vesicle bilayers to liquid crystalline and gel phase lipid bilayers (the slower $R_\perp$, not the $R_\parallel$, is the relevant parameter). This explains also why 5-DS and 16-DS probes, with drastically different rotational dynamics inside micelle and vesicle systems, can produce same or similar maximum DNP enhancements. Therefore, 5-DS and 16-DS are probing the same fluid volumes inside oleate micelles and inside oleate vesicles. We can conclude that the DNP contrast observed for different molecular environments (dispersed, micelles versus vesicles) is predominantly due to differences in the coupling factor, $\rho$, and that our measurements sensitively report about the hydration and water fluid dynamics of the local volume that the spin label is probing. This is an important observation because the coupling factor is the fundamental DNP variable, which is not accessible through NMR relaxation and cw ESR measurements.

Here, it is worth noting the fundamentally different contrast provided through NMR relaxation (f) and DNP ($\rho$) measurements, although both rely on dipolar interaction between $^1$H nuclear spin and radical unpaired electron spin. Overall the leakage factor has shown to be not a key variable in this study, but we do systematically observe a somewhat larger f in vesicles compared to micelles for equal spin label concentrations. This is opposite to an intuitive expectation because spin labels should be more shielded from water in vesicles, and therefore less effective in relaxing water protons. However, in-depth literature studies [72-74] report about very effective spin diffusion and cross relaxation effects across ordered soft matter, such as cell or vesicle membranes, which explains our observation. The difference is that build-up of non-equilibrium $^1$H-water polarization (i.e. DNP effect) can only occur through direct dipolar interactions with the radicals, but relaxation to equilibrium $^1$H-water polarization can occur through direct collision with radicals as well as neighboring protons that indirectly experience cross relaxation from remote radicals.

Figure 15:
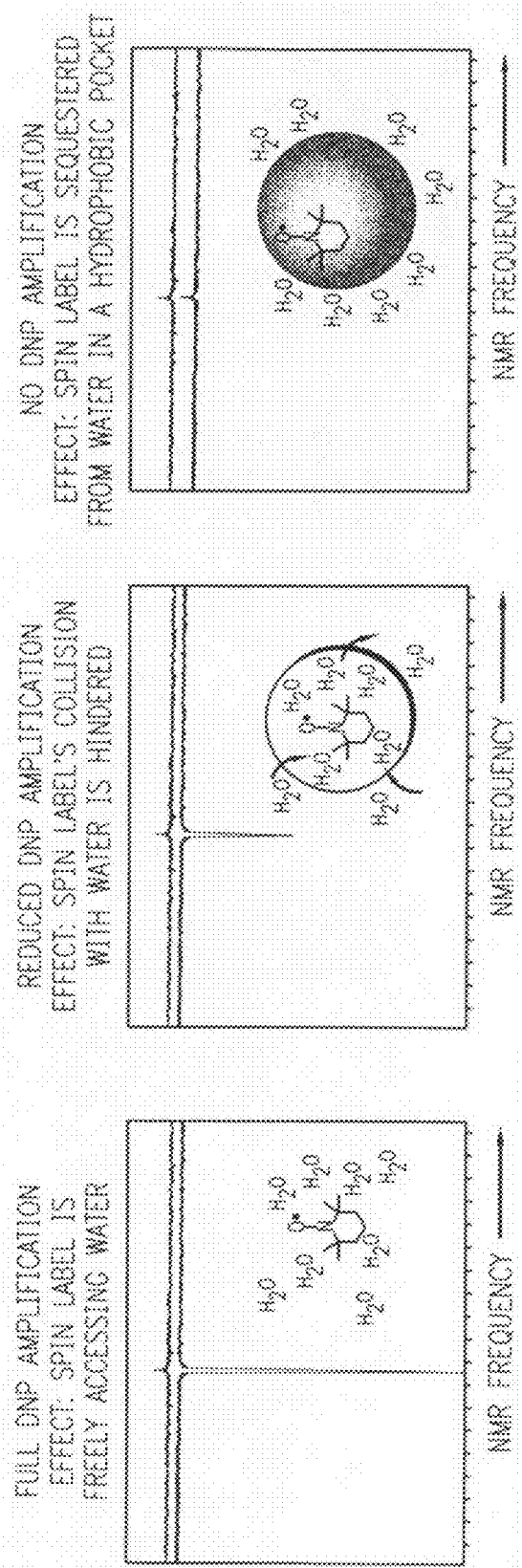
FIG. 15 is plot and schematic of simplified scenarios of possible correlations between the DNP enhancement of $^1$H water NMR signal and the interaction between nitroxide spin probes and water.

We propose three simplified scenarios that will cause differences in the value of $\rho$ for $^1$H DNP contrast: (1) the radical is freely moving in a solution-like environment, (2) the radical is trapped inside a water-permeable soft molecular container where molecular diffusion is hindered due to the more crowded, viscous, environment, and (3) the radical is sequestered into a dehydrated local environment. FIG. 15 is plot and schematic of simplified scenarios of possible correlations between the DNP enhancement of $^1$H water NMR signal and the interaction between nitroxide spin probes and water. If the spin probe is freely dissolved in water, high DNP enhancement can be expected (A). If the spin label's interaction to water is somewhat reduced, either due to decreased water concentrations or due to lower fluid viscosity, the DNP enhancement will be diminished accordingly (B). If the spin label is completely protected from water in a hydrophobic environment, there will be no DNP enhancement (C).

Dispersed surfactant solution. The first situation, where the radical is freely moving in a solution-like environment is applicable to dissolved radical in water or solutions containing dispersed oleate surfactants or other molecules. In solution state we determined the coupling factor of 4-Oxo-2,2,6,6-tetramethyl-1-piperidinyloxy (4-oxo-TEMPO) to be ~0.22 [57, 62]. 5-DS or 16-DS spin labels in dispersed oleate solution would also fall into this category, but the extremely low cmc (35 µM for 5-DS) for both stearic acid spin labels suggests that a micellar phase is created at the employed 300 µM concentration. ESR analysis shows high surfactant mobility and a high hyperfine coupling constant value of $a_N=15.74$ that represents hydrophilic environments, while we observe reduced DNP enhancements with $\rho \cdot s_{max}=0.04$-$0.07$ compared to true solution state. One possible explanation is that we observe a stearic acid micellar phase with rapid surfactant exchange in and out of the micelles, but displaying overall reduced water contact for the surfactants and spin labels. Another possibility is that $s_{max}$ is smaller than 1 (e.g. close to 0.4 as for nitroxide molecules in solution at 300 μM) for 5-DS and 16-Ds in the dispersed oleate phase, which can be due to their faster isotropic rotational diffusion (Table 2), leading to less efficient nitroxide's nitrogen nuclear spin relaxation, thus less efficient mixing of hyperfine states.

Oleate micelles. The second situation applies to the 25 mM oleate samples at pH>10.5 conditions, under which oleate micelles are the dominant species. Water protons in micelles show $E_{max}=-6.9\pm0.5$ and $\rho \cdot s_{max} \sim \rho = 0.12 \pm 0.01$ when employing 5-DS probes and $E_{max}=-6.3\pm0.7$ and $\rho \cdot s_{max} \sim \rho = 0.10 \pm 0.01$ when employing 16-DS probes, so values for both spin probes are within error. The absolute enhancement values of $E_{max}$ is small for both samples because the radical concentration is low, leading to low leakage factors (f~0.11 instead of the maximum value of f~1), and obviously, due to the lower coupling factor compared to pure solution samples.

Before we proceed with the quantification of the coupling factor in terms of fluid dynamics parameters, we first need to discuss the dynamic nature of oleate micelle species that allow for rapid exchange of water in and out of the micelles with sub-nanosecond water residence times inside the micelles. So, within the relevant time scale for DNP build-up (~2 s), all water molecules in and outside the micelles on average have interacted with the spin labels. However, because all spin labeled surfactants are fully incorporated inside the micelles with significantly longer residence time compared to water, the observed DNP enhancement amplitude is determined by the fluid dynamics characteristics inside the micelle systems. So, we do measure average fluid dynamic properties of water from inside the micelle systems, and thus cannot differentiate between interfacial versus core water characteristics, but we do not average over properties of bulk water outside and local water inside the micelles. This is the difference between employing freely diffusing spin label species versus ones that are functionalized onto molecules that become part of the molecular assembly. So, a decrease of the coupling factor, ρ, from 0.22 to 0.10 (or 0.12) can be attributed to an increase of the translational correlation time of water from $\tau_t=76$ ps to $\tau_t=118$ ps (ρ=0.10; 16-DS) or 153 ps (ρ=0.12; 5-DS), according to calculations discussed and shown in FIG. 9 (dotted lines).

The increase in translational correlation times is either because the distance of closest approach between the unpaired electron and the $^1$H of water, d, is increasing or the diffusion coefficient of the local water $D_I$ or the radical $D_S$ within the probing volume of the spin probe is decreasing (Eq. 7). Because the diffusion of water, $D_I$, is significantly greater than the diffusion of the spin probes attached to the surfactants, $D_S$, changes in the diffusion coefficients are mainly attributed to $D_I$. The diffusion coefficient of detached small radical molecules, even in bulk water solution, is about an order of magnitude smaller than that of water, which was determined by diffusion ordered NMR spectroscopy to be $4.1 \cdot 10^{-10}$ m$^2$/s for small nitroxide radicals compared to water's diffusion coefficient of $2.3 \cdot 10^{-9}$ m$^2$/s (data not shown). Eq. 7 predicts that even if the radical became completely immobilized (i.e. $D_S=0$), this would only lead to <10% change in the translational correlation time, if $D_I$ remains unchanged. Also, the fact that the very different rotational dynamics of the spin probes (16-DS vs. 5-DS) did not affect the $^1$H DNP enhancement of water makes it unlikely that the observed DNP effect is due to differences in $D_S$ and/or the ability of the radical to migrate in and out of the micelle. The observation of significant DNP enhancements with ρ=0.1-0.12 inside the micelle volume supports one view within the ongoing debate in the literature about water content in micelles, namely that the interior of oleate micelles are or can be well hydrated [46]. Therefore, it is not likely that there is an increase in d, the van der Waals distance between the water and the mobile spin label interacting inside hydrated micelles compared to free solution. Since we have established that the decreased DNP enhancement is due to increased translational correlation times from 85 ps to 153-181 ps, and that the decreased diffusion coefficient, $D_I$, of the water is the main contributor (Eq. 7), we can conclude that the fluid microviscosity (η) inside the micelles is increased by 80-112% because $\tau_t \propto 1/D_I \propto \eta$, (Eq. 7). Given the bulk water diffusion coefficient (at 22° C.) to be $2.3 \cdot 10^{-9}$ m$^2$/s and viscosity to be 1 cP, the diffusion coefficient of the local water in the oleate micelles can be calculated to be between $1.08 \cdot 10^{-9}$-$1.27 \cdot 10^{-9}$ m$^2$/s with a fluid microviscosity between 1.8-2.11 cP [46]. From this range of viscosities, we believe that the true fluid viscosity inside the oleate core is closer to the 1.8 cP value that originates from measurements using the 5-DS spin probes, because 5-DS displays slower rotational dynamics compared to 16-DS (compare $R_\perp$ in Table 2), which implies that $s_{max}$ is closer to 1. In any case, such increase of local fluid viscosity by 80-112% compared to bulk water is much smaller than previous reports that suggest a 4-fold increase in the oleate micelle core's microviscosity [46]. We believe that this discrepancy originates from the fact that surfactant chain dynamics and water dynamics must neither be linearly nor in any other direct fashion correlated. Further, we have shown with detailed cw ESR spectral analysis, that the rotational diffusion of the surfactant chain is not only anisotropic, but also probe dependent, as shown in our study for the 5-DS and 16-DS probes inside the micelles (Table 2).

Oleate vesicles. The third situation applies to the 25 mM oleate samples at pH ~7.5, where vesicles composed of hydrophobic bilayer structures are the dominant species. When the radicals are sequestered in a dehydrated hydrophobic environment the radical no longer directly interacts with the water protons, eliminating the possibility of dipolar relaxation-mediated DNP as the distance of closest approach (d) becomes very large (Eq. 7). We measure a very small $E_{max}=-0.6\pm3$ with 16-DS, leading to ρ=0.011±0.002, and a slightly higher $E_{max}=-1.4\pm0.1$ with 5-DS, leading to ρ=0.015±0.001. While both values are one order of magnitude smaller than those of micelles, still the 5-DS measures a slightly higher coupling factor than 16-DS, which is possibly due to the closer proximity between 5-DS label and the exterior water, and thus somewhat shorter distance of closest approach. Another possibility is that a very small number of water molecules are penetrating into the area close to the interface, as is also suggested for the Triton X-100 system (discussed below). Yet another hypothetical possibility is that static water remains in the membrane, silent to DNP, due to extremely small $D_I$. However, contradictory to this hypothesis, ESR analysis shows considerable rotational freedom of the spin probes in both micelle and vesicle structures (Table 2); therefore it is unlikely that stationary water is present in the vesicle bilayers. This demonstrates how cw ESR and $^1$H DNP both need to be employed as complementary tools in order to conclude that vesicle bilayer cores are excluded from solvent water, yet considerable surfactant chain dynamics persist. It is important to note that this represents a simple system where data interpretation is straightforward because the location of the spin label is depleted of solvent water. However, for other vesicle systems that may contain some solvent water with slow water exchange characteristics in and out of the bilayer systems, the interpretation of DNP observation can be more complex because one may measure average viscosity properties, and then, effects of slow exchange needs to be taken into account using appropriate models.

Mixed phase of oleate micelles and vesicles. The discussed characteristics of the oleate micelles and vesicles are further supported by our experimental observations that the hyperfine coupling constant, $a_N$, from cw ESR (FIG. 12) as well as $^1$H DNP analysis (FIG. 13) show the expected trend for a series of samples with varying fractions of micelle and vesicle. Here, the decrease in both the $^1$H DNP enhancements and the hyperfine coupling constant $a_N$ (14.75 for pure vesicles and 15.5 for pure micelles) as the vesicle fraction increases, can be attributed to exclusion of solvent water and removal of hydrogen bonding from the vesicle fraction. This is further supported by studies of Marsh et al. [30, 75] on doxyl spin probes in bilayer structures stating that $a_N$=14.5 G corresponds to the absence of hydrogen bonding and $a_N$=15.7 G to fully hydrated samples. However, $a_N$ is sensitive in a complex fashion to both the polarizing field of neighboring molecular moieties (i.e., the effect of the local dielectric permittivity) and the extent of hydrogen bonding by water molecules around the nitroxide spin label because all of these factors influence the unpaired electron spin density on the nitrogen [18]. Also, the decreasing $a_N$ trend matches that of decreasing hyperfine anisotropy that arises from increasing rotational amplitude, so that concurrent changes of chain dynamics can be misinterpreted as changes in polarity and water content [29, 30, 45, 76]. Many reference measurements at low temperature and high field as well as in-depth modeling are required to draw definitive conclusions about the origin of changes in $a_N$ [29, 76]. However, for the system discussed in this work, trends in the hyperfine coupling constant agree with what we observe through $^1$H Overhauser DNP effects. We can directly attribute changes in the $^1$H NMR signal amplification to reduced water fluid viscosity (through $D_f$) inside micelles and the exclusion of water (d→∞) as vesicle bilayers are formed, since s, f and $D_S$ are excluded as variables.

Anhydrous micelles. Continuous wave ESR studies on Triton X-100 micelles show that there is considerable mobility in the core, but less compared to oleate micelle cores, possibly due to crowding effects. The Triton X-100 molecules have a branched 8-carbon tail as opposed to oleate molecules with 18 carbons, leading to a considerably reduced micelle size. The DNP-induced $^1$H NMR signal enhancement of water measured through 16-DS spin probes incorporated in Triton X-100 micelles shows a very small, but still measurable, factor of −1 fold and ρ=0.018. This small, residual, DNP effect on water is either due to minor water penetration through the phenyl region of Triton X-100 micelles, or a small fraction of 16-DS spin labels probing the bulk water phase as they are either not fully incorporated into the micelles or migrate in and out of the micelles. However, given that the ESR analysis shows a homogeneous population, and we operate at concentrations >>cmc, the former is much more likely.

CONCLUSIONS

Figure 8:
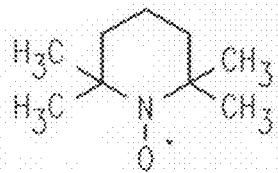
FIG. 8 is a schematic sketch that shows example hydrated materials, where nitroxide spin labels (see stick figure and chemical drawing) can be attached, as described in the invention, to specific sites on the surface and interior of a variety of molecules, molecular assemblies and soft matter. A particular strength of our DNP NMR approach as described in this invention is that large proteins, molecular assemblies or cells, that are conventionally difficult to study by NMR because of signal overlap and large background signal, can be readily studied by our DNP NMR approach. We can utilize site directed mutagenesis of proteins and spin labeling of cystein aminoacids or use spin labels that are covalently functionalized on specific lipid or surfactant molecular positions, which spin labeled molecule can be incorporated into molecular assemblies, such as micelles, vesicles or lipid membranes. This technique is extensively used in electron spin resonance spectroscopy. However, it is novel to employ dynamic nuclear polarization using this specifically spin labeled molecules to study the local water dynamics at the specific molecular site of interest on the surface and interior of hydrated materials. This figure illustrates example hydrated materials that are particularly well suited to be studied by our DNP-amplified NMR approach for selective water detection, but our invention is not limited to the application to this materials. The attachment of spin labels to specific molecular sites is illustrated by a sparse stick-and-a-dot probes incorporated into the example hydrated materials. The top panel on the left illustrates that proteins in solution as well as membrane proteins embedded in lipid and surfactant materials can be studied. The top panel on the right shows that protein aggregation—a hallmark of many neurodegenerative diseases—can be studied at the early stage of aggregation and assembly. The two bottom panels illustrate that micelles, vesicles as well as planar bilayers composed of lipid or surfactant molecules can be studied by our DNP NMR method upon incorporation of spin labeled lipid or surfactant molecules into the assembly.
Figure 8:
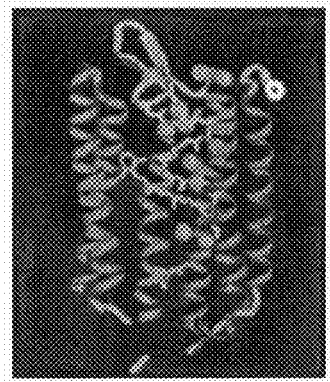
Figure 8:
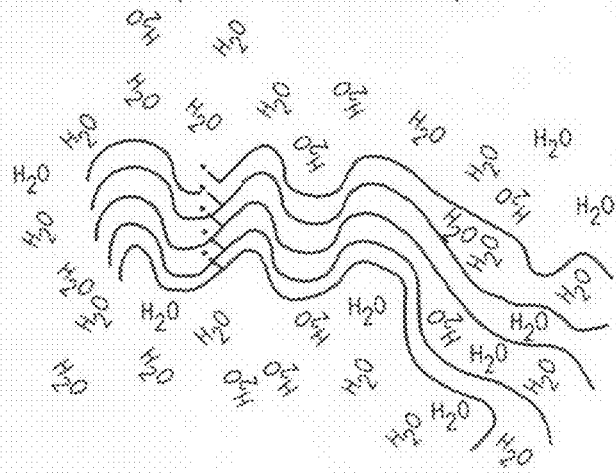
Figure 8:
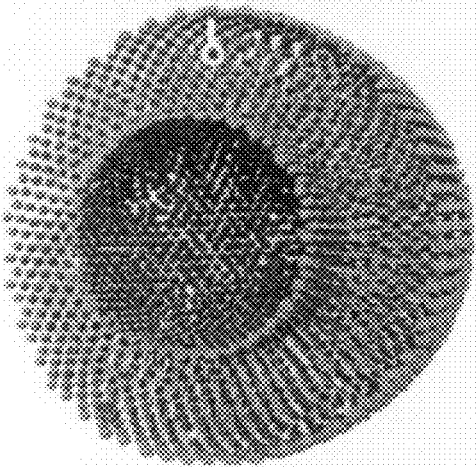
Figure 8:
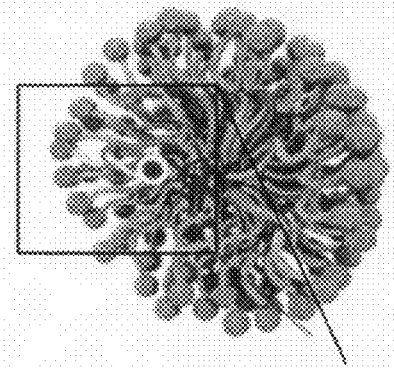

We have presented in this embodiment a unique and powerful DNP-enhanced $^1$H NMR tool for water fluid dynamics studies of soft molecular structures using functionalized and incorporated spin labels. We have demonstrated that our $^1$H DNP analysis tool is capable of measuring local water content and dynamics inside micelle and vesicle assemblies in bulk solutions when combined with cw ESR and $^1$H NMR relaxation analysis, which method can be expanded to the analysis of other hydrated materials through the employment of site specific spin labeling, as illustrated in FIG. 8. The translational fluid dynamics of local water is an important parameter in many molecular assemblies, especially for drug delivery and other biological applications, but is often difficult to experimentally access. Conventional NMR analysis suffers from the lack of spectroscopic contrast between local and bulk water, and conventional ESR analysis lacks direct molecular information. $^2$H quadrupolar NMR analysis, ESR and ESEEM techniques have shown to provide quantitative information on water penetration in frozen micelles and ordered membranes, but not the bulk solvent viscosity information and the dynamic monitoring of assembly processes. ESR does not directly provide translational correlation times of the solvent or other molecules interacting with the spin probe, yet it can directly measure the rotational (and more indirectly the translational) correlation time of the spin probe itself, which can be used to estimate microviscosities of the polymer chains that compose the soft matter. Our methods as described in this embodiment, Overhauser type $^1$H DNP measurements, on the other hand, can directly provide the translational correlation times of the fluid water molecules that interact with the spin labels by targeting the small volume of interest via site-specific spin labels. The combination of $^1$H DNP, ESR, and NMR relaxation analysis were able to conclude that oleate micelles are hydrated with increased local water viscosity of 1.8 cP, while the vesicle bilayer structure is depleted of free water.

$^1$H DNP analysis promises to be a widely applicable tool for fluid dynamics analysis of other soft molecular assemblies. A practical advantage is that our $^1$H DNP instrumentation can be added to a standard cw X-band ESR spectrometer with minor instrument modification [62], which is particularly useful for the combined analysis of cw ESR, NMR relaxometry and $^1$H DNP. The unique strength of our $^1$H DNP tool is that experiments can be performed on solution samples, under ambient conditions and with ~1 s time resolution, so that monitoring of dynamic events, such as protein aggregation, membrane assembly or the formation of hydrophobic cores with gradual water exclusion or changes in fluid dynamics becomes possible.

Materials and Methods

Sample preparation. Spin-labeled micelle and vesicle solutions were prepared as previously described by Fukuda et al. [46] Both 16-DS and 5-DS (Sigma Aldrich) were introduced as spin probes. First, 25 mM sodium oleate (Sigma Aldrich) was dissolved in water and the pH adjusted to the desired value. 16-DS or 5-DS was dissolved in acetone and 300 nmols were aliquotted into tubes. The acetone solvent was evaporated off and then the 16-DS or 5-DS were resuspended in 1 mL of oleate solution. The final pH of each sample was measured to check for changes with the addition of the acidic spin-probes. The samples were then sonicated for 15 s and equilibrated at room temperature for 12-18 hours. The same sample preparation process was used for 100 mM Triton X-100 (Sigma Aldrich). Samples or solvents were not degassed.

Continuous wave ESR spectroscopy. ESR spectra were acquired on a Bruker EMX X-band spectrometer at 295K equipped with a rectangular $TE_{102}$ cavity using a center field of 0.35 Tesla and microwave frequency of 9.8 GHz. Typically, a modulation amplitude of 0.12 Gauss, a modulation frequency of 100 kHz and a field sweep range of 100 Gauss were used. A fused silica capillary of 0.7 mm inner diameter was used as the sample tube, and was sealed with beeswax on both ends.

DNP-enhanced $^1$H NMR spectroscopy. DNP-enhanced NMR experiments were carried out using the ESR instrument under similar conditions as described for cw ESR experiments. A home-built U-shape NMR coil made of 0.013-inch diameter, Teflon coated silver wire (A-M Systems, Inc.) was introduced into a tuned and matched $TE_{102}$ ESR cavity [62]. The use of thin wire and a straight coil inside the ESR cavity is important to ensure that the ESR remains tuned and matched upon insertion. The coil is connected via twisted wires and coaxial cable to a simple LC tuning box tuned to 14.8 MHz and connected to a broadband channel of a Bruker Avance NMR spectrometer. During DNP operation, the ESR cavity remains tuned at a quality factor (Q) of about 3000 while the unpaired electrons are irradiated with a power output between 25 mW and 25 W. We recently showed that for sample setups and volumes as employed here, there is minimal sample heating effects when using up to 2 W of incident microwave power [62]. The maximum DNP enhancement ($E_{max}$) was experimentally determined for each sample by measuring E while varying the applied microwave power, and then extrapolating to infinite power using Eqns. 1 and 4. First, a cw ESR spectrum is recorded to determine the frequency and field at which one of the three ESR lines of the nitroxide spin labels should be irradiated. Then, the amplified $^1$H NMR spectra are recorded with on-resonant ESR microwaves at varying $B_1$ field strengths. The enhancement is computed relative to the NMR spectrum without microwave irradiation, and the enhancement factor plotted against power (P). Equation is 4 is then used with equation I to determine the maximum possible enhancement by extrapolating the results to infinit power.

Third Embodiment

We have demonstrated above that DNP can add important complementary information to ESR on spin-labeled biomolecules as well as provide unique analysis and imaging capabilities. Overall, DNP amplification modulations are gaining increasingly more attention for various applications that require enhanced sensitivity and/or information contrast. Therefore, the descriptions of how to easily add DNP capability to the most commonly available commercial cw X-Band setup, and also how to build an optimized portable DNP setup, are key information in order to be able to carry out the DNP NMR analysis through hyperpolarized water, as described in this invention.

Here, we report DNP experiments carried out using our custom X-band DNP transmitter, using the commercial cavity and electromagnet system, with which $^1$H signal enhancement of ~130 fold have been obtained for water. We also present our completely portable X-band DNP system, where the ultimate goal was to perform DNP experiments in the field, especially in clinical laboratories of our collaborators. This goal has been realized by replacing the electromagnet with a permanent magnet, where −92 fold amplification was achieved. The discrepancy in signal enhancement when using the permanent magnet as opposed to the electromagnet comes from the field strength of the permanent magnet not precisely matching the ESR resonance condition within the narrow bandwidth of the cavity, which can be solved when employing a field-adjustable permanent magnet or tuneable cavity. Also a horn/reflector combination was used for microwave irradiation, but only gave an enhancement factor of 8.2. This small value is due to inefficient transmission and collection of the $B_{1e}$ field into the sample container. The current design can be significantly improved.

A novel feature of the new DNP amplification and EPR detection device is the X-band driver. Two separate technologies come together uniquely to tailor the driver for DNP and EPR performance: (1) high-power and high-speed X-band amplifiers, and (2) high-speed, low-loss X-band switches. For the cw DNP amplification and EPR experiments, the high power, stable frequency output and wide tuning range is most important. However, as soon as pulsed-DNP and EPR experiments are to be employed, the switching and reaction speed of the X-band driver's components is the key factor for optimum performance for pump-probe, saturation recovery and other pulsed DNP and EPR experiments.

Figure 16:
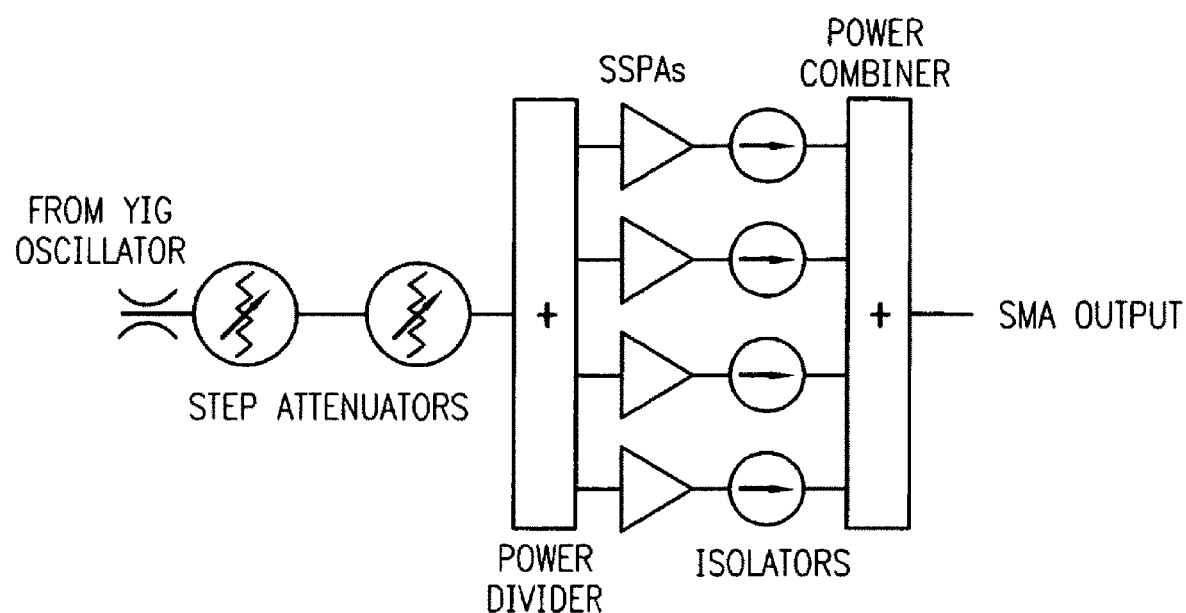
FIG. 16 depicts a fast solid-state switch together with a power amplifier setup used in the invention.

The X-band driver is capable of power amplification of >10 W, in cw mode, and if needed, high speed switching at the time scale of 1 ns or less. The block diagram of the pulsed transmitter is shown in FIG. 16. To achieve power levels of 10 W or beyond without creating exorbitant cost or packaging complexities, the source utilizes "corporate" power dividing and re-combining as shown. The modest power level from a solid-state YIG-tuned oscillator is connected to the driver through a step attenuator, high-speed solid-state switch, and a second step attenuator. It is then divided into N equal-power ports using an N-way Wilkinson power divider or similar passive component. The output ports of the divider are coupled directly to N separate SSPAs, each having an output power capacity between ~+37 and +40 dBm (5 to 10 W). To protect the SSPAs and for pulse-integrity, each SSPA is connected to a coaxial isolator having an isolation in X band of at least 25 dB. The output of the N isolators is then fed into a N-way Wilkinson power combiner or similar passive component. The output port of the power combiner is connected to a directional coupler and then to the EPR/DNP apparatus under use. The coupled port is connected to a variable attenuator and then a fast envelope detector, preferably a zero-bias Schottky diode detector.

In addition to the corporate power combining, the other key aspect of the driver design shown in FIG. 16 is a fast solid-state switch. The enabling technology is a pseudomorphic high-electron mobility transistor (pHEMT). These combine short switch rise- and fall-times with (typically of 10 ns or less) with very low insertion loss (typically 2 dB or less). Because the switch is located in the circuit where the power level is modest (20 mW or less), it can be activated and de-activated very quickly without saturation or other nonlinear effects that would occur if the switch were located at a point of higher power (100 mW or more).

Another key aspect of the present invention is that the SSPA output waveform is a faithful reproduction of the input waveform without significant distortion or dispersion. This requires only that the activation pulse width, $t_p$, be somewhat longer than the impulse response time of the SSPAs in the corporate combining circuit. From Fourier-transform theory, this impulse response time can be no shorter than the reciprocal instantaneous bandwidth $1/\Delta f$ of the SSPAs. Fortunately, the bandwidth of "standard" MMIC-based SSPAs is typically 2 GHz or greater, so that the impulse response time is roughly 0.5 ns.

In a preferred embodiment, the EPR/DNP driver shown in FIG. 16 can be improved in two ways. First, the SSPAs can be improved in performance substantially by changing the MMIC materials from GaAs (or InP)-based transistors to GaN-based transistors. Recent developments at UCSB, Cree Research, and other Companies have shown good amplifier efficiencies at X band from GaN-based SSPAs but at power levels far exceeding those from GaAs (or InP)-based devices.

A second improvement is in the implementation of the solid-state switch control. Experience has shown that the speed of GaAs-based pHEMT switches is limited more by the control circuit than the switch itself. So changing the control logic from TTL to ECL (emitter-coupled logic) can reduce the pulse width to below 1 ns, as low as 300 ps.

The driver in FIG. 16 has important practical advantages over standard EPR and related X-band designs. First, it utilizes "standard" SSPAs such as those widely used in cw SATCOMM applications. These are much less expensive and stable than specialized X-band "pulse" amplifiers. Second, through the use of modern pHEMT switches, the activation can then be done by a standard, TTL-based pulse generator with nanosecond pulse-width capability.

EPR detection has been built and used before by other researchers and companies such as Bruker and Varian in a conceptually similar fashion, but implementation of EPR detection as a modular option to a portable DNP device as well as the EPR detector as a portable device by itself is a novel capability. The EPR spectrum can be detected indirectly, by measuring the DNP enhancement to the NMR signal as the microwave frequency is varied. The plot of NMR enhancement vs. the microwave frequency is proportional to an absorption EPR spectrum, and can be treated as such, as long as the dipolar coupling or scalar coupling induced Overhauser mechanism is effective to cause DNP. The indirect detection method can be automated. The microwave frequency can be incremented and set by the NMR program through TTL trigger synchronization with the NMR signal detection.

Results and Discussion

Figure 17:
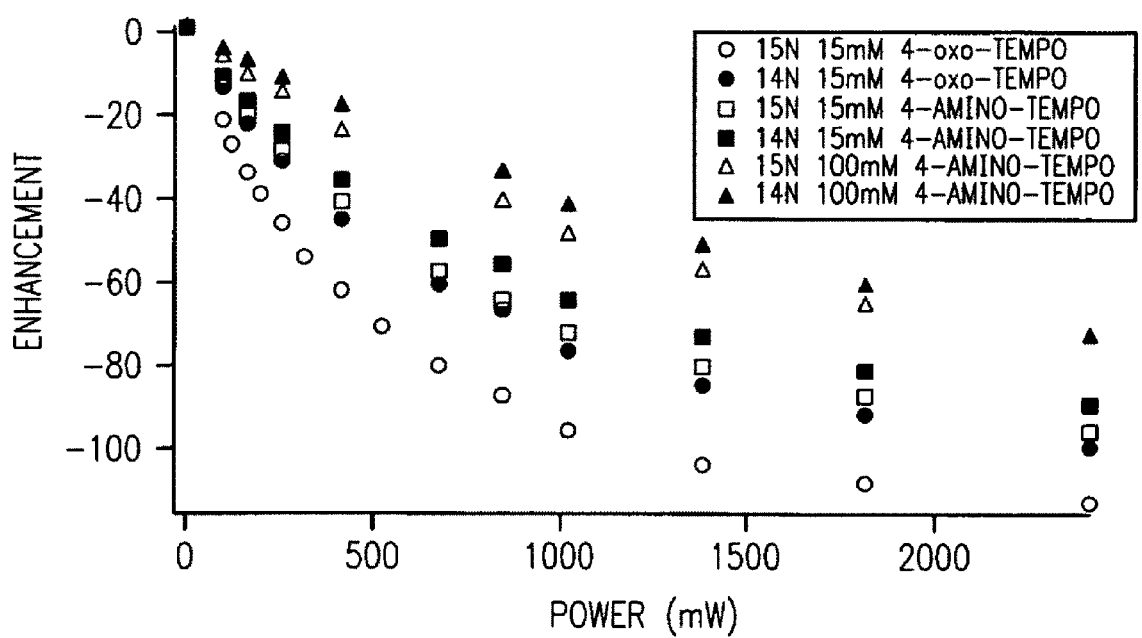
FIG. 17 shows measured enhancements vs. microwave power for six different samples using our custom X-band transmitter and $TE_{102}$ resonant cavity in an electromagnet.

Using the commercial Bruker $TE_{102}$ cavity and microwave source (see Experimental below for more details), $^1$H signal enhancements of water of −73±2 have been measured with 15 mM $^{15}$N 4-oxo-2,2,6,6-tetramethylpiperidine-1-oxyl (4-oxo-TEMPO) while operating the X-band bridge (Bruker Biospin) in the unleveled mode which has a maximum output power of 800 mW (all enhancements discussed will be for $^1$H of water). Enhancements as high as −55 have been measured while operating the bridge at only 200 mW in leveled mode. In situations where the spin-labeled biomolecules possess narrow lines that can be easily saturated, the commercial cw ESR spectrometer provides sufficient output power to obtain maximum attainable DNP enhancement, and can therefore be employed for full DNP analysis without compromised performance. At fairly high concentrations, which have broad ESR lines, the measured enhancements at 800 mW are well below the maximum possible as seen in FIG. 17, indicating that more microwave power was needed. In each of these experiments, air was flowed over the sample to prevent significant sample heating. It is evident from these curves that the electron spin transition is not being fully saturated and there is room for improvement by increasing the irradiation power. Using our homebuilt microwave source and the Bruker resonance cavity, $^1$H signal enhancements of water with TEMPO near the theoretical maximum were achieved.

Our studies estimate the ultimate maximum enhancement of 4-oxo-TEMPO at high concentrations, where f and $s_{max}$ are both ~1, to be approximately −140. This was found to be independent of whether natural abundance $^{14}$N or isotope enriched $^{15}$N 4-oxo-TEMPO was used, as Heisenberg exchange negates the advantage using a radical with fewer ESR lines [98].

Differences in ESR linewidths of the different radicals can affect the actual achieved enhancements, but not $E_{max}$. Therefore, with sufficient microwave power available and at sufficiently high concentrations, we should measure nearly equal enhancements for $^{14}$N and $^{15}$N versions of 4-oxo-TEMPO and 4-amino-TEMPO as well as for very high concentrations of radicals. The data in table 3 shows this to be true, and indicates we can nearly saturate radical concentrations as high as 15 mM while the ESR lines of 100 mM nitroxide radical are too broad to fully saturate even with our custom X-band driver.

TABLE 3

| Stable radical | conc (mM) | ESR $\Delta B_{pp}$ (gauss) | $E_{measured}$ | $E_{max}$ | cooling air |
| --- | --- | --- | --- | --- | --- |
| 15N 4-oxo*TEMPO | 15 | 1.15 | −131 ± 6 | — | no |
| 15N 4-oxo TEMPO | 15 | 1.15 | −112 ± 4 | −136 ± 8 | yes |
| 14N 4-oxo TEMPO | 15 | 1.57 | −98 ± 3 | −131 ± 8 | yes |
| 15N 4-amino TEMPO | 15 | 1.6 | −94 ± 4 | −127 ± 8 | yes |
| 14N 4-amino TEMPO | 15 | 2.33 | −88 ± 3 | −126 ± 6 | yes |
| 15N 4-amino TEMPO | 100 | 7.35 | −72 ± 3 | −121 ± 9 | yes |
| 14N 4-amino TEMPO | 100 | 7.72 | −71 ± 3 | −124 ± 10 | yes |

The advantage of using a resonant cavity in an electromagnet is that the magnetic field can be easily adjusted to precisely meet the ESR resonance condition of the given radical so that efficient $B_{1e}$ transmission to the sample is ensured. If the given sample and NMR probe device can be accommodated into the cavity and portability is not an issue, this set up is most versatile to easily achieve near theoretically optimum DNP enhancement. However, a resonant cavity has a narrow bandwidth so that its frequency has to be adjusted to meet the resonance condition. An electromagnet, however, is so large and heavy that it cannot be moved even within our lab setting. To achieve portability for certain applications or to facilitate collaboration with laboratories that offer specific expertise or capabilities we need a transportable permanent magnet.

Permanent magnets whose fields are mechanically adjustable were very recently developed [100, 101] (but not yet commercialized) where the easy-to-use but narrow-band resonant cavity can be employed to precisely adjust to on-resonant ESR conditions. However, due to ease of availability, we acquired a permanent magnet (Aster Enterprises, Inc.) whose field is set to 0.3487 T, as this fixed value is close to the resonance transition of dissolved nitroxide radicals in our cavity and NMR probe setup. When employing a 100 mM 4-Amino-TEMPO solution, the spectrum has significant intensity at 0.3487 Tesla although not precisely on resonance due to its broad ESR lines, significant $^1$H enhancement of water of −92±11 was achieved in the permanent magnet. This increase in enhancement from −70 to −92 is due to sample heating as cooling air was not used in the portable set up. This decreases τ, thus increasing ρ, which relationship is discussed in the second embodiment in detail.

Figure 18:
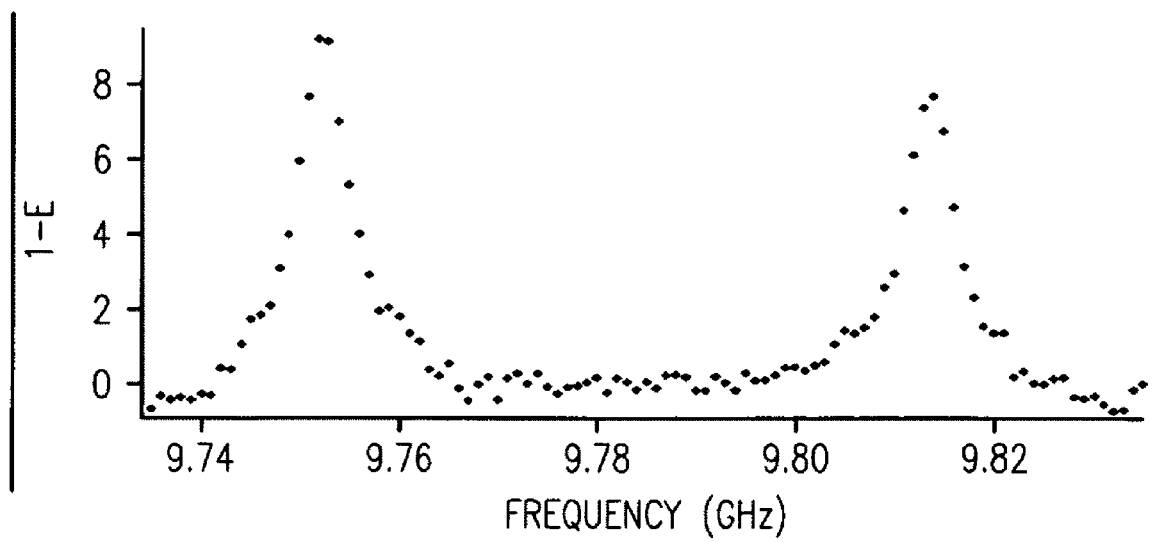
FIG. 18 shows the 1-enhancement (E) vs. frequency plot acquired using our custom X-band transmitter (a) coupled to a $TE_{102}$ resonant cavity with the variable-field electromagnet set to the resonance field of one of the ESR transitions of $^{15}$N 4-oxo-TEMPO and (b) coupled to our horn and reflector setup in the permanent, fixed field magnet.

While a −92 fold enhancement in the resonant cavity using our permanent magnet is considerable, this setup lacks versatility as different samples may or may not be near the resonance condition. In order to improve the versatility of our portable DNP device, we employed a horn and reflector combination inside the permanent magnet to concentrate the Bie field into the sample area. This setup should have a lower and adjustable quality factor, and thus a wider and adjustable frequency bandwidth. As our home-built transmitter has a wide frequency tuning capability over the range of (8-10 GHz), the combination with such a horn/reflector setup will allow the study of a wide range of radicals and samples with different ESR resonance frequencies with this portable setup. This feature can be seen in FIG. 18, where the microwave frequency is swept at a fixed magnetic field while detecting DNP-enhanced NMR signal. After finding the optimum frequency to excite an ESR transition, the position of the reflector was adjusted until maximum DNP enhancement was reached. Currently, the largest $^1$H enhancement measured in this setup is only −8.2±2 using 15 mM $^{15}$N 4-oxo-TEMPO, far below that obtained in the resonant rectangular cavity. However, this system has yet to be optimized. Using a cylindrical horn and reflector setup, Wind and Ardenkjaer-Larsen obtained a ten fold $^1$H signal enhancement at 1.4 Tesla using a triarylmethyl (trityl) based free radical [102].

Figure 19:
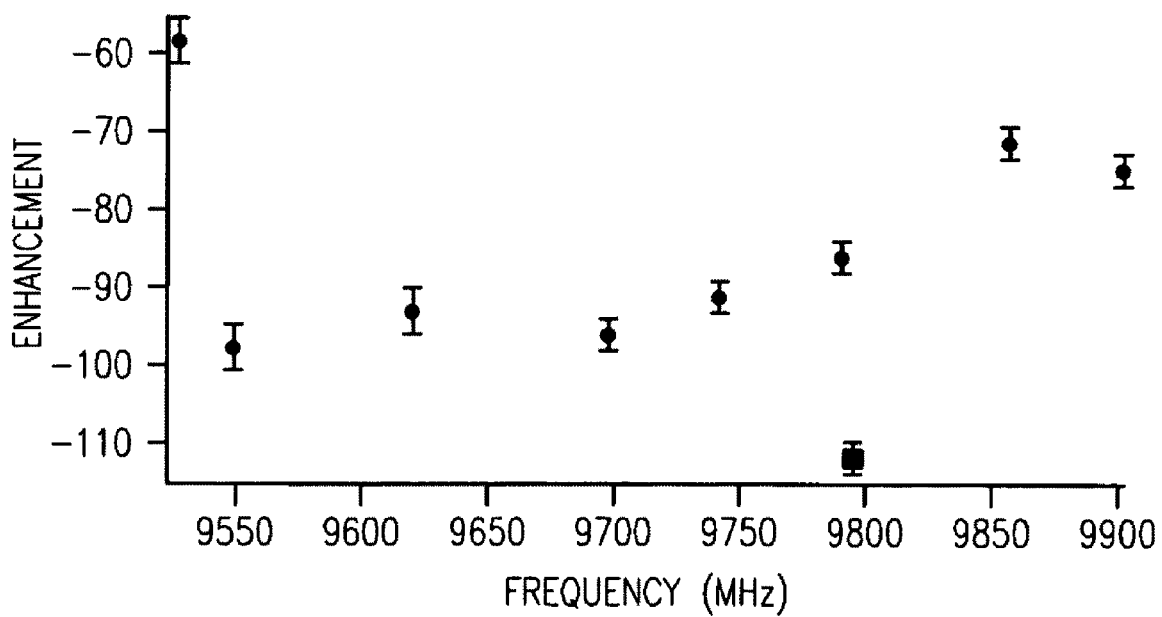
FIG. 19 shows the enhancement factors for a sample of 15 mM $^{15}$N 4-oxo-TEMPO in water with 2 W of power from our custom X-band transmitter. The filled circles represent the enhancement measured with our tunable $TE_{102}$ cavity which has a tuning range of 200 MHz, while the square point represents the enhancement from the commercial $TE_{102}$ cavity with a much narrower tuning range.

Our commercial $TE_{102}$ resonant cavity was modified so that the resonant frequency could be made tunable for its use in the fixed field permanent magnet. This was realized by making the wall opposite along which the microwave is coupled in via the wave guide (the long axis of the resonator) adjustable with a copper plate attached to a non-magnetic screw. A non-magnetic spring was placed between the moveable wall and a fixed plate attached to the cavity. By turning the screw, the copper plate can move further in or out of the resonator, thus varying the length of the cavity and resonant frequency. The frequency at which the cavity was resonating was monitored using the Bruker EMX spectrometer and EIP frequency counter. Our custom microwave source was then coupled to the cavity, set to the resonant frequency of the cavity, and the DNP enhancement measured. Enhancements were measured over a range of 9902.5 MHz to 9528.5 MHz, corresponding to a change in field from 3522 gauss to 3389 gauss, which were the mechanical limits of our modified cavity. By changing the length of the cavity, the location in the cavity at which the maximum $B_{1e}$ field is transmitted changes, which results in reduction of DNP enhancements, as the sample is in a fixed position inside the cavity. This effect can perhaps be seen in FIG. 19 which shows the measured DNP enhancement factors versus frequency. Over a large frequency range of nearly 200 MHz, greater than −90 fold enhancements were measured with the maximum enhancement being −98 fold. An enhancement of −112 was measured for the same sample in the unmodified commercial cavity. This experiment shows we are able to reach a wide and useful tuning range by a small modification of the commercial Bruker $TE_{102}$ cavity. This modified cavity can be readily employed with a fixed-field magnet and tunable microwave source to perform DNP experiments.

Alternatively, we used the commercial resonator inside a field adjustable Halbach magnet. As before, the frequency at which the cavity resonates was determined using the Bruker EMX spectrometer and EIP frequency counter. The resonant frequency of the cavity depends on the NMR probe and sample holder being incorporated into its core, but if these are not altered the frequency is precisely reproducible. Thus, once adjusted and optimized, the EMX spectrometer and frequency counter are not necessary parts of the equipment that needs to be transported with the portable setup. An SMA to waveguide adapter was attached directly to the cavity as it would not fit into the magnet when coupled via the waveguide. The magnetic field was adjusted to match the ESR condition of a $^{15}$N 4-oxo-TEMPO sample in aqueous solution determined by the frequency at which the cavity resonates. A $^1$H enhancement was measured of −80±15 under conditions where no sample heating is expected. This is lower than the −112 measured in the electromagnet, which is due to the difficulty of saturating inhomogeneously broadened ESR lines caused by spatial field distributions across the volume of the sample that is not centered at the field.

CONCLUSION

X-Band is the most commonly used frequency bandwidth for ESR studies. As ESR and DNP analysis of solution state samples both critically depend on the dynamics of the radical or spin label, DNP at X-band together with ESR experiments can provide valuable information about the local environment of the spin label as well as dynamics of the labeled molecule itself. A commercial ESR spectrometer can easily be used to perform DNP experiments, provided a simple NMR spectrometer allowing for 14.8 MHz experiments is available. With this setup, significant signal enhancements as well as quantification of key DNP parameters can be achieved. By monitoring changes in the enhancement amplitude of the $^1$H signal of water with spin labeled biological molecules, information about the local accessibility and viscosity of water at or near the spin label can be obtained, providing new information compared to straightforward ESR detection or NMR relaxation analysis.

For experiments where large signal enhancements are preferred or required such as in a RELIC experiment for perfusion contrast imaging, a relatively inexpensive home-built microwave transmitter device is capable of reaching near full saturation of broad ESR lines. $^1$H enhancements at 0.35 T of up to 130 fold have been measured. In a RELIC experiment, this not only increases the image contrast and sensitivity, but also the observation time for which the flow can be monitored from administration to detection [89]. This homebuilt microwave source can be coupled into a tunable resonant cavity or a horn/reflector device. A resonant cavity is more efficient at transferring power to the sample, but a tunable horn antenna offers more versatility for performing experiments with different samples when used with a fixed magnetic field as it offers a much wider frequency bandwidth for signal transmission. Our goal to build a portable DNP polarizer has been achieved with $^1$H enhancements up to −92 fold thus far. The entire portable system fits onto a cart and has been taken to different buildings across campus for demonstration experiments, providing great versatility and the ability to take our DNP analysis tool or polarizer to the lab of collaborators.

Experimental

Sample Preparation. The free radicals 4-oxo-2,2,6,6-tetramethyl-1-piperidinyloxy (4-oxo-TEMPO) and 4-amino-2,2,6,6-tetramethyl-1-piperidinyloxy (4-amino-TEMPO) were purchased from Sigma-Aldrich. Isotope enriched $^{15}$N labeled 4-oxo-TEMPO was purchased from Cambridge Isotope Laboratories. $^{15}$N labeled ammonia and $D_6$-acetone were purchased also from Cambridge Isotope Laboratories and used to synthesize $^{15}$N labeled 4-Amino-TEMPO following published procedures [103-107]. 4-Amino-Tempo was dissolved directly into de-ionized water while 4-oxo-TEMPO was initially dissolved at a high concentration into DMSO and then diluted into de-ionized water, the final solution containing no more than 5% DMSO by volume. Volumes of approximately 5 uL were loaded into 0.7 mm inner diameter silica capillaries and sealed with beeswax and used for both ESR and NMR measurements.

DNP with commercial X-Band ESR equipment. Successful DNP experiments have been realized using a rectangular $TE_{102}$ resonant cavity at ~9.8 GHz with a microwave bridge (EF 041 MR) in a 0-1.5 Tesla electromagnet, controlled by an EMX ESR spectrometer (all from Bruker Biospin). For NMR detection, an Avance 300 NMR spectrometer (Bruker Biospin) as well as a much less expensive and portable Kea NMR spectrometer (Magritek Limited) was used. Also, for NMR detection, an RF coil that allows the resonant cavity to remain highly tuned (Q>2000) while placed inside the cavity needs to be used. Therefore, the advantage of a resonant ESR cavity needs to be fully exploited if DNP experiments are to be carried out with standard cw ESR equipment. A high Q of 2000-3000 inside the cavity was maintained when using a coil and sample holder made of a quartz capillary and a small piece of chlorinated Teflon (CTFE), which holds the silica capillary and is pierced with channels to thread through the thin silver wires to form a double U-coil. Variable capacitors are used for the tune and match and the coil serves as the inductor. An SMA cable connects the probe to a tuning box which contains the tune and match capacitors which is connected to an NMR spectrometer. Loosely wrapped 2-4 turn solenoid coils also have been employed for our DNP experiments when higher NMR detection sensitivity was needed, however the double U-coil allows the resonant cavity to tune to a higher Q more consistently, thus is optimized for DNP performance. A home built resonant LC circuit tuned to ~14.8 MHz with a tuning range of about 5 MHz was built using 120 pF variable capacitors from Voltronics (TM120C), with the double U-coil (or solenoid coil) serving as the inductor. This home built coil allows for both ESR and NMR measurements of aqueous solutions along with DNP experiments performed under cw microwave irradiation, all without moving the sample.

DNP with the custom X-band transmitter and commercial resonator. While the use of a commercial ESR spectrometer for DNP is an extremely useful tool, and can be very well utilized for quantitatively characterizing the DNP effect, the output power is insufficient for optimum DNP performance when a sample has broad ESR lines. Before carrying out the DNP experiment, a cw ESR spectrum is taken using the previously described sample holder and NMR coil to determine the precise resonance field of the electron transition. The resonance frequency of the cavity is monitored with an EIP 548A frequency counter. Without other alterations, the resonant cavity was disconnected from the Bruker X-band bridge and connected to our homebuilt X-band transmitter device, while the magnetic field was set to the field of the resonance to be saturated. The microwave source is turned on, and the frequency of the YIG adjusted to the previously determined resonance frequency of the cavity. The frequency at which the cavity resonates is very reproducible as long as the same NMR probe and sample holders are used, but changing either of these can change the resonance frequency significantly.

Portable DNP Setup. To achieve a portable DNP setup, a 0.3487 (at 22.5° C. with temperature variance of ~0.025%/° C.) Tesla permanent magnet was purchased from Aster Enterprises, Inc. This magnet is relatively small in size and transportable (~150 pounds), and has a large opening (35 mm gap) to comfortably place X-band microwave equipment (tunable resonant cavity or horn/reflector) and an NMR probe with sample inside. The main field is perpendicular to the gap and normal to the two flat poles. The custom X-band driver was coupled to the tunable $TE_{102}$ cavity. Alternatively, we also used an X-band 10 dBi horn instead of a cavity, purchased from Instruments for Industry (SH90-10), with a moveable aluminum plate employed as the reflector. The horn/reflector combination has a much bigger tuning frequency range in comparison to the tunable $TE_{102}$ cavity. A horn/reflector device provides for much more versatility if bulky sample holders need to be employed, easy sample access or manipulation is needed or large samples that greatly affect the quality factor are examined. Overall, there is much room for improving the performance of microwave transmission in free space by better focusing the $B_{1e}$ field to the sample, by using a circular horn and optimum reflector geometries.

NMR detection was realized using the U-coil probe with the portable Kea NMR spectrometer, as previously discussed. The ESR spectrum is indirectly detected via the measurement of DNP enhancement as a function of transmission frequency. We used the software program Labview 7.0 along with a USB-DAQ board (LabJack U12) to control the YIG synthesizer via the DAQ board's digital IO interface. To record DNP enhancement vs. frequency, the Kea spectrometer was programmed to send a TTL pulse through the DAQ to the waiting Labview program, which then changed the frequency, followed by an NMR experiment on the Kea. A macro was written to automate the process and record the entire DNP enhancement vs. frequency spectrum automatically, which indirectly measures an ESR absorption spectrum, as seen in FIG. 18b). The entire system fits onto a cart and only requires a power outlet to perform experiments. A laptop computer controls the frequency output of the YIG and the NMR spectrometer.

The complete device package that can perform DNP-enhanced NMR and MRI consists of the (a) tunable $TE_{102}$ cavity, high-power X-band transmitter, (b) permanent magnet, (c) horn/reflector based or another kind of resonator for microwave transmission to the sample located in the magnet, (d) radio-frequency NMR probe with gradient coils if performing a MRI experiment, (e) portable NMR spectrometer and (f) modular ESR detector.

In accordance with a particular embodiment, a core package comprises the (a) tunable, high-power X-band transmitter, (c) tunable $TE_{102}$ cavity or horn/reflector based resonator for microwave transmission to the sample located in the magnet, and (d) radio-frequency NMR probe, as other components can be readily obtained from commercial sources.

Components (a), (c), (d) and (f) are devices for which components can be purchased from vendors and assembled together following our invented design. The assembly of (a) is a novel design that has never been put together in a similar fashion before by others. Component (b) can be purchased from Aster Enterprises, Inc. or other companies that offer similar products. The device parts (c), (d) and (f) have been built and used before by other people in a conceptually similar fashion, but their method of use and implementation into our complete device is novel. Component (e) can be purchased from Magritek Limited, Tecmag or other NMR spectrometer companies.

The invention can be used for in vivo MRI of cardiovascular perfusion in the heart, brain and other organs by utilizing perfectly harmless and contaminant-free hyperpolarized water as a contrast agent, where signal amplification of the infused saline solution (or plasma) can be realized. Images can be provided of cerebral blood flow with better contrast and resolution than conventionally possible to accurately diagnose acute stroke situations. The production of hyperpolarized water as a contrast agent relies on the use of the invented device and/or concept. Also, the determination of brain death, which is a very difficult and questionable process, can be facilitated by a methodology to measure the degree of brain perfusion with higher sensitivity and contrast than conventionally feasible.

In accordance with an embodiment of the invention, the transmitter can be packaged into a laptop size hard-case so that the input and output of the device can be interfaced by rugged SMA, SMB and other electronic and electrical connectors. The magnet can be encased in a sturdy wood casing with appropriate windows and lids, which not only enhances the safety when transporting and using the magnet, but also improves temperature stability, and therefore the field stability, of the magnet. A tunable $TE_{102}$ cavity or horn/reflector combination mounted on a sturdy and adjustable aluminum frame that can be easily slid into the magnet and locked in, so that the positioning with respect to the magnet center is easily reproducible. The radio-frequency probe can be made mechanically rugged so that no parts of the LC circuit are movable, which ensures its function and lifetime.

REFERENCES

1. D. G. Nishimura, A. Macovski, J. M. Pauly, *IEEE Transactions on Medical Imaging.* 3, 140 (1986).
2. J. Granwehr, E. Harel, S. Han, S. Garcia, L. Chavez, A. Pines, *Phys. Rev. Lett.* 95, 075503 (2005).
3. P. T. Callaghan, *Principles of Nuclear Magnetic Resonance Microscopy*, (Oxford University Press, New York, 1991).
4. W. Overhauser, *Phys. Rev.* 92, 411 (1953).
5. T. R. Carver, C. P. Slichter, *Phys. Rev.* 92, 212 (1953).
6. K. H. Hausser, D. Stehlik, *Adv. Mag. Res.* 3, 79 (1968). C. P.
7. A. Abragam, *The Principles of Nuclear Magnetism* (Clarendon, Oxford, England, 1961).
8. Slichter, *Principles of Magnetic Resonance*, (Springer-Verlag, Berlin, 1989).
9. R. A. Wind, *Prog. Nucl. Magn. Reson. Spectrosc.* 17, 33 (1985).
10. L. R. Becerra, G. T. Gerfen, T. J. Temkin, D. J. Singel, R. G. Griffin, *Phys. Rev. Lett.* 71 (1993) 3561-3564.
11. J. H. Ardenkjaer-Larsen, B. Fridlund, A. Gram, G. Hansson, L. Hansson, M. H. Lerche, R. Servin, M. Thaning, K. Golman, *Proc. Nat. Acad. Sci.* 100 (2003) 10158-10163.
12. D. J. Lurie, D. M. Bussel, L. H. Bell, J. R. Mallard, *J. Magn. Reson.* 76 (1988) 366-370
13. D. Grucker, *Magn. Reson Med* 14 (1990) 140-147.
14. Bechinger, B.; Seelig, *J. Chem. Phys. Lipids* 1991, 58, 1-5.
15. Ernst, J. A.; Clubb, R. T.; Zhou, H. X.; Gronenborn, A. M.; Clore, G. M. *Science* 1995, 267, 1813-1817.
16. Fernandez, C.; Hilty, C.; Wider, G.; Wuthrich, K. *Proc. Natl. Acad of Scis. USA* 2002, 99, 13533-13537.
17. Gawrisch, K.; Gaede, H. C.; Mihailescu, M.; White, S. H. *Eur. Biophys. J. Biophy.* 2007, 36, 281-291.
18. Griffith, O. H.; Dehlinge. Pj; Van, S. P. *J. Membrane Biol.* 1974, 15, 159-192.
19. Ho, C.; Slater, S. J.; Stubbs, C. D. *Biochemistry* 1995, 34, 6188-6195.
20. Huster, D.; Jin, A. J.; Arnold, K.; Gawrisch, K. *Biophys. J.* 1997, 73, 855-864.
21. Malmsten, M. *Soft Matter* 2006, 2, 760-769.
22. Kwok, C. S.; Mourad, P. D.; Crum, L. A.; Ratner, B. D. *J. Biomed. Mater. Res.* 2001, 57, 151-164.
23. Nasongkla, N.; Shuai, X.; Ai, H.; Weinberg, B. D.; Pink, J.; Boothman, D. A.; Gao, J. M. *Angew. Chem. Int. Ed.* 2004, 43, 6323-6327.
24. Gaede, H. C.; Gawrisch, K. *Biophys. J.* 2003, 85, 1734-1740.
25. Bagchi, B. *Chem. Rev.* 2005, 105, 3197-3219.
26. Ge, M. T.; Freed, J. H. *Biophys. J.* 2003, 85, 40234040.
27. Finer, E. G.; Darke, A. *Chem. Phys. Lipids* 1974, 12, 1-16.
28. Khoshtariya, D. E.; Hansen, E.; Leecharoen, R.; Walker, G. C. *J. Mol. Liq.* 2003, 105, 13-36.
29. Kurad, D.; Jeschke, G.; Marsh, D. *Biophys. J.* 2003, 85, 1025-1033.
30. Marsh, D. *Proc. Natl. Acad. of Scis. USA* 2001, 98, 7777-7782.
31. Marsh, D. *Eur. Biophys. J. Biophy.* 2002, 31, 559-562.
32. Furo, I. *J. Mol. Liq.* 2005, 117, 117-137.
33. Bryant, G.; Pope, J. M.; Wolfe, J. *Eur. Biophys. J. Biophy.* 1992, 21, 223-232.
34. Hawton, M. H.; Doane, J. W. *Biophys. J.* 1987, 52, 401-404.
35. Volke, F.; Pampel, A. *Biophys. J.* 1995, 68, 1960-1965.
36. Xu, Z. C.; Ellena, J. F.; Cafiso, D. S. *Biophys. J.* 1986, 49, A508-A508.
37. Horst, R.; Wider, G.; Fiaux, J.; Bertelsen, E. B.; Horwich, A. L.; Wuthrich, K. *Proc. Natl. Acad. of Scis. USA* 2006, 103, 15445-15450.
38. Bratt, P. J.; Kevan, L. *J. Phys. Chem.* 1993, 97, 7371-7374.
39. Borbat, P. P.; Costa-Filho, A. J.; Earle, K. A.; Moscicki, J. K.; Freed, J. H. *Science* 2001, 291, 266-269.
40. Costa, A. J.; Shimoyama, Y.; Freed, J. H. *Biophys. J.* 2003, 84, 2619-2633.
41. Gaffney, B. J.; Marsh, D. *Proc. Natl. Acad. of Scis. USA* 1998, 95, 12940-12943.
42. Bartucci, R.; Erilov, D. A.; Guzzi, R.; Sportelli, L.; Dzuba, S. A.; Marsh, D. *Chem. Phys. Lipids* 2006, 141, 142-157.
43. Erilov, D. A.; Bartucci, R.; Guzzi, R.; Shubin, A. A.; Maryasov, A. G.; Marsh, D.; Dzuba, S. A.; Sportelli, L. *J. Phys. Chem. B* 2005, 109, 12003-12013.
44. Szajdzinskapietek, E.; Maldonado, R.; Kevan, L.; Jones, R. R. M. *J. Am. Chem. Soc.* 1984, 106, 4675-4678.
45. Owenius, R.; Engstrom, M.; Lindgren, M.; Huber, M. *J. Phys. Chem. A* 2001, 105, 10967-10977.
46. Fukuda, H.; Goto, A.; Yoshioka, H.; Goto, R.; Morigaki, K.; Walde, P. *Langmuir* 2001, 17, 4223-4231.
47. Overhauser, A. W. *Phys. Rev.* 1953, 92, 411-415.
48. Dorn, H. C.; Wang, J.; Allen, L.; Sweeney, D.; Glass, T. E. *J. Magn. Reson.* 1988, 79, 404-412.
49. Hausser, K. H.; Stehlik, D. *Adv. Magn. Reson.* 1968, 3, 79-139.
50. Bates, R. D.; Drozdoski, W. S. *J. Chem. Phys.* 1977, 67, 4038-4044.
51. Potenza, J. *Adv. Mol. Relaxation.* 1972, 4, 229-354.
52. Borah, B.; Bryant, R. G. 1981, 75, 3297-3300.
53. Ardenkjaer-Larsen, J. H.; Laursen, I.; Leunbach, I.; Ehnholm, G.; Wistrand, L. G.; Petersson, J. S.; Golman, K. *J. Magn. Reson.* 1998, 133, 1-12.
54. Barros, J. W.; de Souza, R. E.; Engelsberg, M.; Golman, K.; Ardenkjaer-Larsen, J. H. *Appl. Phys. Lett.* 2002, 80, 160-162.
55. Barros, W.; Engelsberg, M. *J. Magn. Reson.* 2007, 184, 101-107.
56. Nicholson, I.; Lurie, D. J.; Robb, F. J. L. *J. Magn. Reson. B* 1994, 104, 250-255.
57. Armstrong, B. D.; Han, S. *J. Chem. Phys.* 2007, 127, 104508.
58. Cistola, D. P.; Hamilton, J. A.; Jackson, D.; Small, D. M. *Biochemistry* 1988, 27, 1881-1888.
59. Reiss-Husson, F.; Luzzati, V. *J. Phys. Chem.* 1964, 68, 3504-3511.
60. Brunner, H.; Hausser, K. H. *J. Magn. Reson.* 1972, 6, 605-611.

61. Robinson, B. H.; Haas, D. A.; Mailer, C. *Science* 1994, 263, (5146), 490-493.
62. Armstrong, B. D.; Lingwood, M. D.; McCarney, E. R.; Brown, E. R.; Bluemler, P.; Han, S. *J. Magn. Reson.* 2008, 191, 273-281.
63. Rehfeld, S. J.; Eatough, D. J.; Plachy, W. Z. *J. Lipid Res.* 1978, 19, 841-849.
64. Israelachvili, J. *Intermolecular & Surface Forces*, 2nd ed.; Academic Press: Santa Barbara, 1991.
65. Waggoner, A. S.; Keith, A. D.; Griffith, O. H. *J. Phys. Chem.* 1968, 72, 4129-4132.
66. Song, L. Y.; Ge, X. W.; Wang, M. Z.; Zhang, Z. C.; Li, S. C. *J. Polym. Sci., Part A: Polym. Chem.* 2006, 44, 2533-2541.
67. Schneider, D. J.; Freed, J. H. *Biol. Magn. Reson.* 1989, 8, 1-76.
68. Budil, D. E.; Lee, S.; Saxena, S.; Freed, J. H. *J. Magn. Reson. A* 1996, 120, 155-189.
69. Stoll, S.; Schweiger, A. *J. Magn. Reson.* 2006, 178, 42-55.
70. Freed, J. H. In *Spin Labeling Theory and Applications*; Berliner, L. J., Ed.; Academic Press: New York, 1976; p 53.
71. Melo, E. C. C.; Costa, S. M. B.; Macanita, A. L.; Santos, H. *J. Colloid Interface Sci.* 1991, 141, 439-453.
72. Bryant, R. G. *Annu. Rev. Phys. Chem.* 1978, 29, 167-188.
73. Fung, B. M.; Mcgaughy, T. W. *Biophys. J.* 1979, 28, 293-303.
74. Zhong, J. H.; Gore, J. C.; Armitage, I. M. *Magn. Reson. Med.* 1990, 13, 192-203.
75. Marsh, D. *Mol. Biol., Biochem. Biophys.* 1981, 31, 51-142.
76. Steinhoff, H. J.; Savitsky, A.; Wegener, C.; Pfeiffer, M.; Plato, M.; Mobius, K. *BBA-Bioenergetics* 2000, 1457, 253-262.
77. A. W. Overhauser, Polarization of Nuclei in Metals. Physical Review 92 (1953) 411-415.
78. A. Abragam, and M. Borghini, Dynamic polarization of nuclear targets. Progr. Low Temp. Phys. (C. J. Gorter, editor. North-Holland) 4 (1964) 384-449.
79. R. A. Wind, M. J. Duijvestijn, C. van der Lugt, A. Manenschijn, and J. Vriend, Applications of dynamic nuclear polarization in $^{13}C$ NMR in solids. Progress in Nuclear Magnetic Resonance Spectroscopy 17 (1985) 33-67.
80. V. Weis, and R. G. Griffin, Electron-nuclear cross polarization. Solid State Nuclear Magnetic Resonance 29 (2006) 66-78.
81. V. S. Bajaj, C. T. Farrar, I. Mastovsky, J. Vieregg, J. Bryant, B. Elena, K. E. Kreischer, R. J. Temkin, and R. G. Griffin, Dynamic nuclear polarization at 9 T using a novel 250 GHz gyrotron microwave source. Journal of Magnetic Resonance 160 (2003) 85-90.
82. J. Wolber, F. Ellner, B. Fridlund, A. Gram, H. Johannesson, G. Hansson, L. H. Hansson, M. H. Lerche, S. Mansson, R. Servin, M. Thaning, K. Golman, and J. H. Ardenkjaer-Larsen, Generating highly polarized nuclear spins in solution using dynamic nuclear polarization. Nuclear Instruments & Methods in Physics Research Section a-Accelerators Spectrometers Detectors and Associated Equipment 526 (2004) 173-181.
83. M. Alecci, I. Seimenis, S. J. McCallum, D. J. Lurie, and M. A. Foster, Nitroxide free radical clearance in the live rat monitored by radio-frequency CW-EPR and PEDRI. Physics in Medicine & Biology 43 (1998) 1899-1905.
84. W. Barros, and M. Engelsberg, Enhanced Overhauser contrast in proton-electron double-resonance imaging of the formation of an alginate hydrogel. Journal of Magnetic Resonance 184 (2007) 101-107.
85. K. Golman, I. Leunbach, J. Stefan Petersson, D. Holz, and J. Overweg, Overhauser-enhanced MRI. Academic Radiology 9 (2002) S104-S108.
86. M. C. Krishna, S. English, K. Yamada, J. Yoo, R. Murugesan, N. Devasahayam, J. A. Cook, K. Golman, J. H. Ardenkjaer-Larsen, S. Subramanian, and J. B. Mitchell, Overhauser enhanced magnetic resonance imaging for tumor oximetry: Coregistration of tumor anatomy and tissue oxygen concentration. Proceedings of the National Academy of Sciences of the United States of America 99 (2002) 2216-2221.
87. J. Lurie David, H. Li, S. Petryakov, and L. Zweier Jay, Development of a PEDRI free-radical imager using a 0.38 T clinical MRI system. Magnetic resonance in medicine: official journal of the Society of Magnetic Resonance in Medicine/Society of Magnetic Resonance in Medicine 47 (2002) 181-6.
88. D. J. Lurie, G. R. Davies, M. A. Foster, and J. M. S. Hutchison, Field-cycled PEDRI imaging of free radicals with detection at 450 mT. Magnetic Resonance Imaging 23 (2005) 175-181.
89. E. R. McCarney, B. D. Armstrong, M. D. Lingwood, and S. Han, Hyperpolarized water as an authentic magnetic resonance imaging contrast agent. *Proc. Natl. Acad. of Scis. USA* 2007, 104, 1754-1759.
90. E. R. McCarney, Han, S., Dynamic Nuclear Polarization Enhanced Nuclear Magnetic Resonance and Electron Spin Resonance Studies of Hydration and Local Water Dynamics in Micelle and Vesicle Assemblies. *Langmuir* (2008) asap. DOI: 10.1021/1a800334k.
91. K. H. Hausser, and D. Stehlik, Dynamic nuclear polarization in liquids. Advances in Magnetic Resonance 3 (1968) 79-139.
92. B. D. Armstrong, and S. Han, A New Model for Overhauser Enhanced Nuclear Magnetic Resonance Using Nitroxide Radicals. *J. Chem. Phys.* 2007, 127, 104508.
93. A. Abragam, The principles of nuclear magnetism, Clarendon Press, Oxford, England, 1961.
94. I. Solomon, Relaxation Processes in a System of 2 Spins. Physical Review 99 (1955) 559-565.
95. I. Nicholson, D. J. Lurie, and F. J. L. Robb, The Application of Proton-Electron Double-Resonance Imaging Techniques to Proton Mobility Studies. Journal of Magnetic Resonance Series B 104 (1994) 250-255.
96. J. A. Weil, J. R. Bolton, and J. E. Wertz, Electron paramagnetic resonance elementary theory and practical applications, Wiley, New York, 1994.
97. W. Muller-Warmuth, and K. Meise-Gresch, Molecular motions and interactions as studied by dynamic nuclear polarization (DNP) in free radical solutions. Advances in Magnetic Resonance 11 (1983) 1-45.
98. R. D. Bates, and W. S. Drozdoski, Use of Nitroxide Spin Labels in Studies of Solvent-Solute Interactions. Journal of Chemical Physics 67 (1977) 4038-4044.
99. I. U. N. Molin, K. M. Salikhov, K. I. Zamaraev, and K. I. Zamaraev, Spin exchange: principles and applications in chemistry and biology, Springer-Verlag, Berlin; New York, 1980.
100. Bauer, C., G. Jeschke, and P. Blümler, A permanent magnet with field-sweep capability for EPR applications, in EUROMAR. 2006: York, United Kingdom
101. Blümler, P., New magnets for mobile NMR and EPR, in 8th International Conference on Magnetic Resonance in Porous Media. 2006: Bologna, Italy.
102. R. A. Wind, and J. H. Ardenkjaer-Larsen, $^1H$ DNP at 1.4 T of water doped with a triarylmethyl-based radical. Journal of Magnetic Resonance 141 (1999) 347-354.

103. B. A. Bates, M. E. Johnson, and B. L. Currie, Stable Isotope Substituted Spin Labels 0.2. An Improved Synthesis of Perdeuterio-N-15-(1-Oxyl-2,2,6,6-Tetramethyl-4-Piperidinyl)Maleimide. Journal of Labelled Compounds & Radiopharmaceuticals 20 (1983) 33-38.
104. K. M. Murayama, Syoji; Yoshioka, Takao; Kurumada, Tomoyuki; Process for preparing triacetonamine, Sankyo Company Limited (Tokyo, JA), United States, 1976.
105. G. M. Rosen, Use of Sodium Cyanoborohydride in Preparation of Biologically-Active Nitroxides. Journal of Medicinal Chemistry 17 (1974) 358-360.
106. E. G. Rozantsev, Free nitroxyl radicals, Plenum Press, New York, 1970.
107. S. K. T. K. K. Yoshizue, Process for preparing Acetonin, Sankyo Company Limited (Tokyo, JA), United States, 1976.

OTHER RELATED ART

S. Han, E. R. McCarney, B. D. Armstrong, "Dynamic Nuclear Polarization Enhanced Magnetic Resonance Analysis of Local Water Dynamics in Soft Molecular Assemblies at 9.8 GHz using Amplified $^1$H Water Signal", Appl. Magn. Reson. 34 (2008) 1-DOI.10.1007.
E. R. McCamey, S. Han, "Spin-labeled gel for the production of radical-free dynamic nuclear polarization enhanced molecules for NMR spectroscopy and imaging", J. Magn. Reson. 190 (2008), 307-315.
S. Han, E. R. McCarney, B. Armstrong, "Polarization matrix for producing radical-free nuclear spin hyper-polarized molecules as contrast agents", provisional U.S. patent application, August 2006.
R. Gitti, C. Wild, C. Tsiao, K. Zimmer, T. E. Glass, H. C. Dorn, J. Am. Chem. Soc. 110 (1988) 2294-2296.
H. C. Dorn, T. E. Glass, R. Gitti, K. H. Tsai, Appl. Magn. Reson. 2 (1991) 9-27.
H. C. Dorn, J. Wang, L. Allen, D. Sweeney, T. E. Glass, J. Magn. Reson. 79 (1988) 404-412.
N. M. Loening, M. Rosay, V. Weis, R. G. Griffin, J. Am. Chem. Soc. 124 (2002) 8808-8809.
C.-G. Joo, K.-N. Hu, J. A. Bryant, R. G. Griffin, J. Am. Chem. Soc. 128 (2006) 9428-9432.
J. H. Ardenkjaer-Larsen, B. Fridlund, A. Gram, G. Hansson, L. Hansson, M. H. Lerche, R. Servin, M. Thaning, K. Golman, Proc. Nat. Acad. Sci. 100 (2003) 10158-10163.
E. Johansson, S. Månsson, R. Wirestam, J. Svensson, J. S. Petersson, K. Golman, F. Ståhlberg, Magn. Reson. Med. 51 (2004) 464-472.
K. Golman, I. Leunbach, J. Stefan Petersson, D. Holz, and J. Overweg, "Overhauser-enhanced MRI" Acad. Radiol. 9 (2002) S104-S108.
I. Nicholson, D. J. Lurie, and F. J. L. Robb, "The Application of Proton-Electron Double-Resonance Imaging Techniques to Proton Mobility Studies", J. Magn. Reson. 104 (1994) 250-255.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A method for treating hydrated material to produce a hyperpolarized substance, in which the hydrated material is in a fluid that contains water, and a stable nitroxide radical spin label is attached to the hydrated material, comprising conducting a dynamic nuclear polarization process on the hydrated material to transfer spin polarization from spin label electrons to water nuclei, whereby to hyperpolarize the water under ambient temperature wherein the dynamic nuclear polarization process is conducted using components comprising a tunable, solid state high power X-band driver, an X-band resonator for microwave transmission to the hydrated material, a radio-frequency nuclear magnetic resonance probe; a portable magnet that contains the hydrated material; a portable nuclear magnetic resonance spectrometer; and an electron spin resonance detector.

2. The method of claim 1 in which the dynamic nuclear polarization process is conducted in a ESR cavity polarization cell that contains the hydrated material wherein the hyperpolarized water is obtained, whereby the nitroxide radical is not freely dissolved in water, but attached to the hydrated material through covalent bonds.

3. The method of claim 2 in which the hydrated material in the polarization cell is agarose material and the nitroxide radical is a derivative of 2,2,6,6-tetramethypiperidine 1-oxyl.

4. The method of claim 3 in which the agarose material is sepharose.

5. The method of claim 2 in which the hydrated material is selected from hydrogel, tentagel, sephadex or modifications of agarose materials.

6. The method of claim 2 in which the nitroxide radical are other stable nitroxide spin labels other than derivatives of 2,2,6,6-tetramethypiperidine 1-oxyl.

7. The method of claim 2 in which the hyperpolarized water is created in continuous flow.

8. The method of claim 2 in which the hyperpolarized water is free of nitroxides.

9. The method of claim 8 in which the hyperpolarized water free of nitroxides, in a pure form or mixed into isotonic saline solution or plasma, is intravenously injected into a living subject with the purpose of obtaining magnetic resonance images of blood flow with enhanced contrast.

10. The method of claim 8 in which the hyperpolarized water free of nitroxides, in a pure form or mixed in isotonic saline solution or plasma, is injected into the carotid artery of a living subject with the purpose of obtaining magnetic resonance images of blood flow with enhanced contrast.

11. The method of claim 2 in which the dynamic nuclear polarization process amplifies the $^1$H NMR signal via electron spins residing on the spin labeled molecules wherein the electrons possess greater than 600 fold higher spin polarization compared to $^1$H nuclei.

12. The method of claim 2 in which the hydrated material is a single molecule or an assembly of molecules, whereby the material can be composed of peptides, proteins, lipid molecules, amphiphilic surfactants, polymers or a mixture of such molecules.

13. The method of claim 2 in which the analysis of the dynamic nuclear polarization performed on hydrated molecules or materials that are specifically spin labeled at targeted sites yield local dynamic parameters, such as the translational correlation times of the nitroxide and water that is in dipolar interaction with the nitroxide, the local diffusion coefficient of water within roughly 10 Å distance of the spin label, the distance of closest approach between the unpaired electron of the nitroxide and the $^1$H nucleus of water.

14. The method of claim 1 for the selective characterization of local water associated with the hydrated material suspended in bulk water, the local water having a $^1$H NMR signature under the application of the dynamic nuclear polarization process, comprising:

covalently attaching nitroxide radicals to targeted sites of the hydrated material to form a functionalized molecule or material that is dissolved in or suspended in water whereby to form spin labeled molecules or materials; and using the dynamic nuclear polarization process to amplify only the $^1$H NMR signal of the local environment of the nitroxide spin label within roughly 10 Å distance.

15. The method of claim 1 in which the electron spin resonance detector has direct electron spin resonance detection capability.

* * * * *